United States Patent [19]
Michelson

[11] Patent Number: 6,142,997
[45] Date of Patent: *Nov. 7, 2000

[54] SURGICAL RONGEUR

[75] Inventor: Gary Karlin Michelson, 438 Sherman Canal, Venice, Calif. 90291

[73] Assignee: Gary Karlin Michelson, Venice, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/905,360

[22] Filed: Aug. 4, 1997

Related U.S. Application Data

[60] Division of application No. 08/337,107, Nov. 10, 1994, Pat. No. 5,653,713, which is a continuation-in-part of application No. 08/108,908, Aug. 18, 1993, which is a continuation-in-part of application No. 07/905,127, Jun. 24, 1992, abandoned, which is a continuation of application No. 07/398,987, Aug. 28, 1989, abandoned, which is a continuation-in-part of application No. 07/341,849, Apr. 24, 1989, Pat. No. 5,009,661.

[51] Int. Cl.[7] .................................................. A61B 17/32
[52] U.S. Cl. .............................. 606/83; 606/170; 606/184
[58] Field of Search ............................... 606/83, 170, 184

[56] References Cited

U.S. PATENT DOCUMENTS

| | | |
|---|---|---|
| 2,984,241 | 5/1961 | Carlson . |
| 3,752,161 | 8/1973 | Bent . |
| 5,061,269 | 10/1991 | Muller ........................................ 606/83 |
| 5,275,607 | 1/1994 | Lo et al. ............................. 606/170 X |
| 5,702,420 | 12/1997 | Sterling et al. ........................ 606/83 X |

*Primary Examiner*—Michael H. Thaler
*Attorney, Agent, or Firm*—Martin & Ferraro, LLP

[57] ABSTRACT

An improved rongeur for cutting bone or cartilage comprising two shaft members capable of reciprocating motion relative to each other wherein one shaft member terminates in a foot plate and the other shaft member comprises a combined cutting element and storage member is disclosed. The combined cutting element and storage member has a cutting edge at its distal end and a storage chamber proximate the cutting edge for collecting and storing cut pieces of bone or cartilage in an amount greater than the maximum bone or cartilage capable of being cut in a single full cut. The combined cutting element and storage member is truly disposable, rather than merely replaceable and requires the use of no tools or special assembly. The rongeur may be manually activated or activated by a solenoid and powered by a battery.

39 Claims, 16 Drawing Sheets

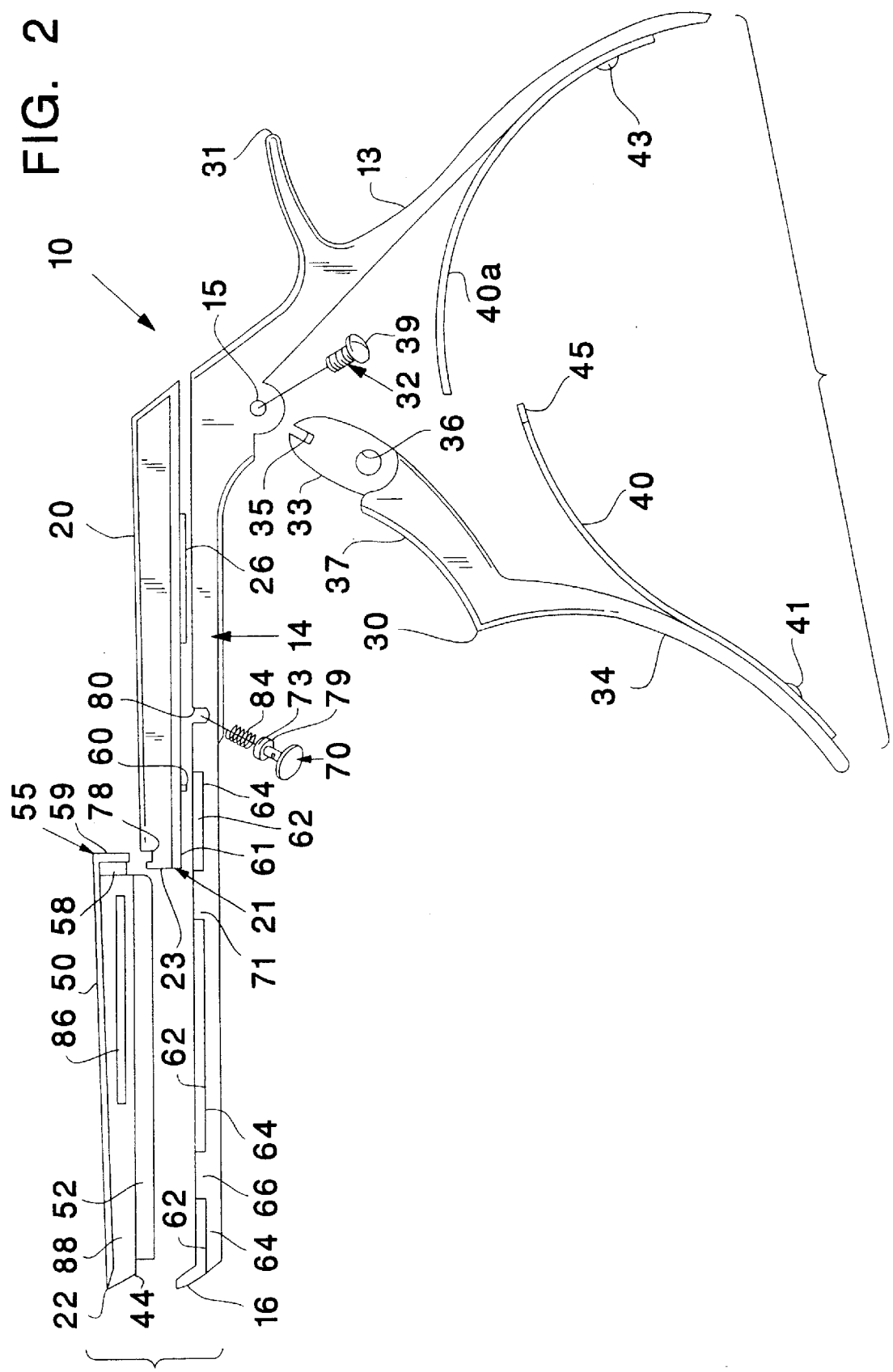

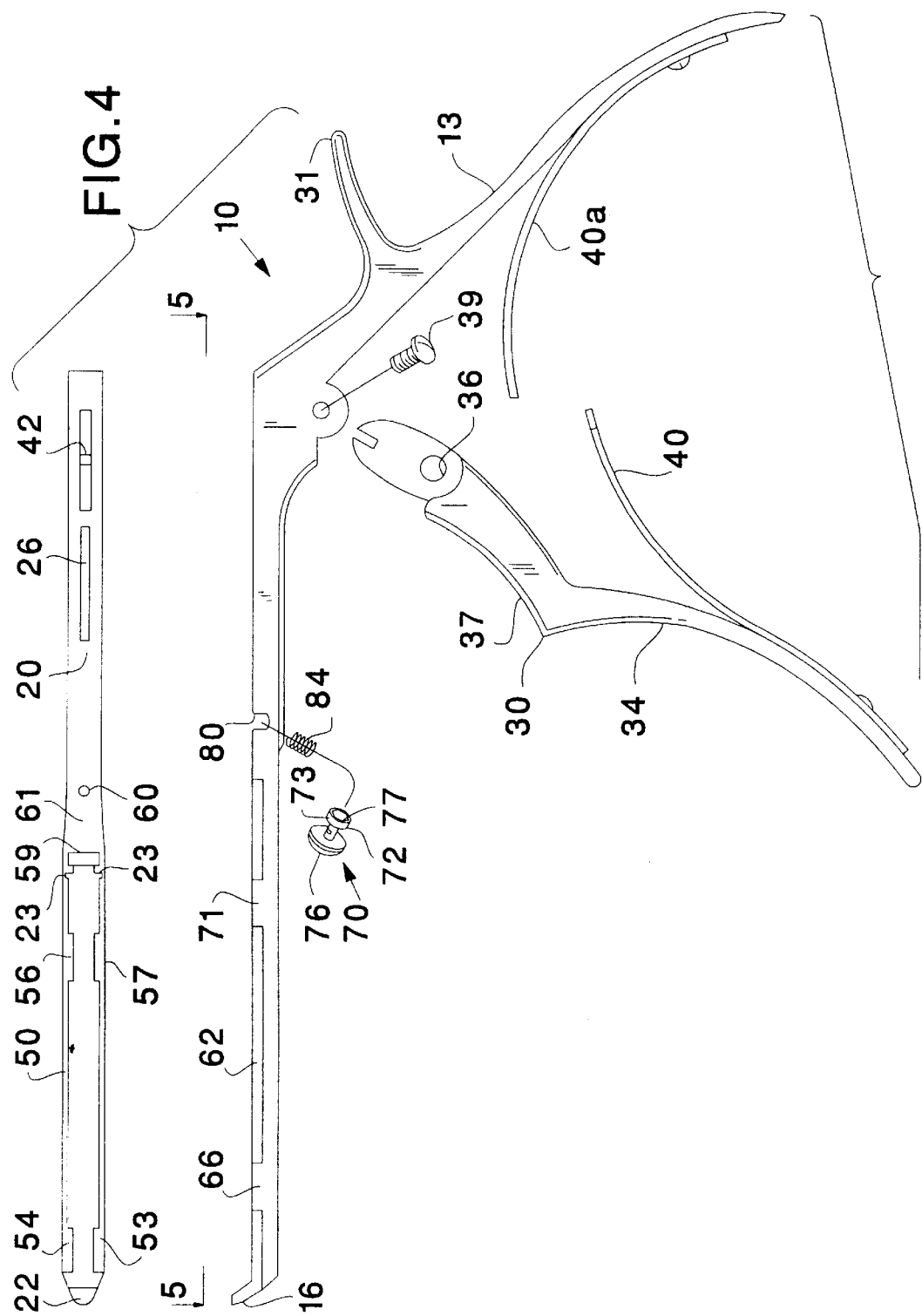

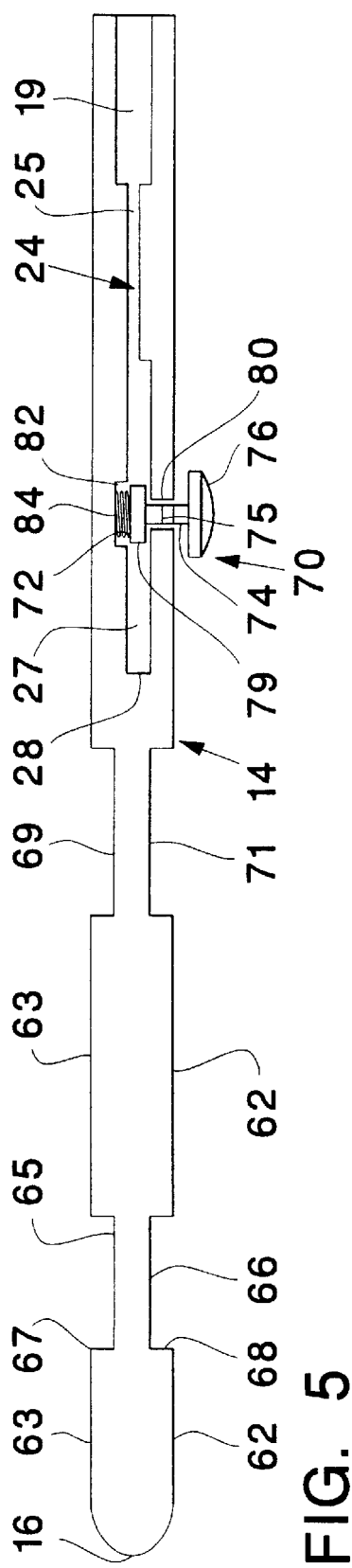
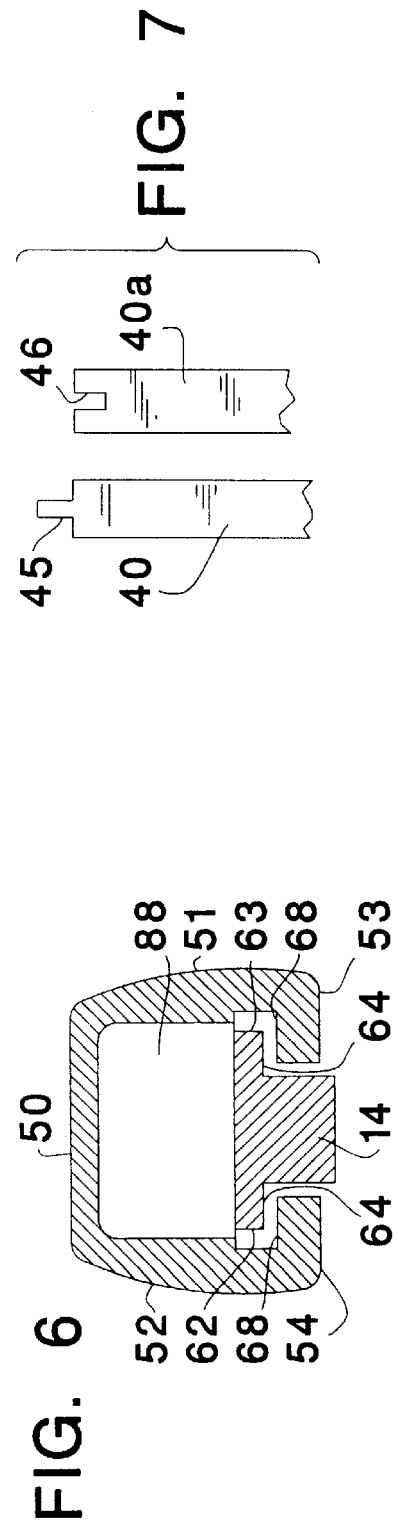
FIG. 5
FIG. 6
FIG. 7

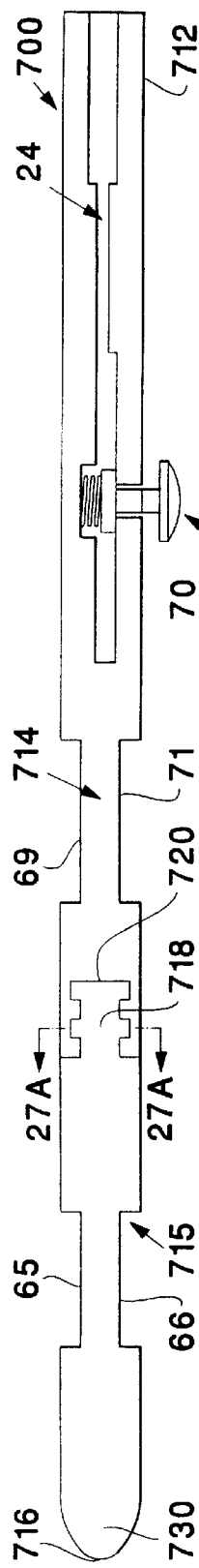
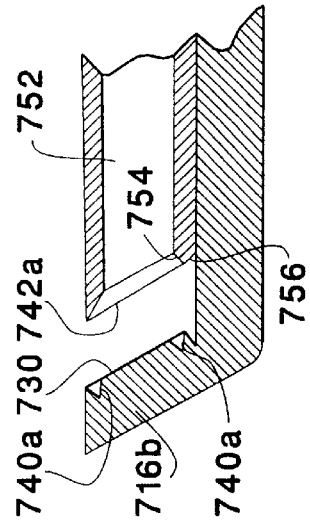
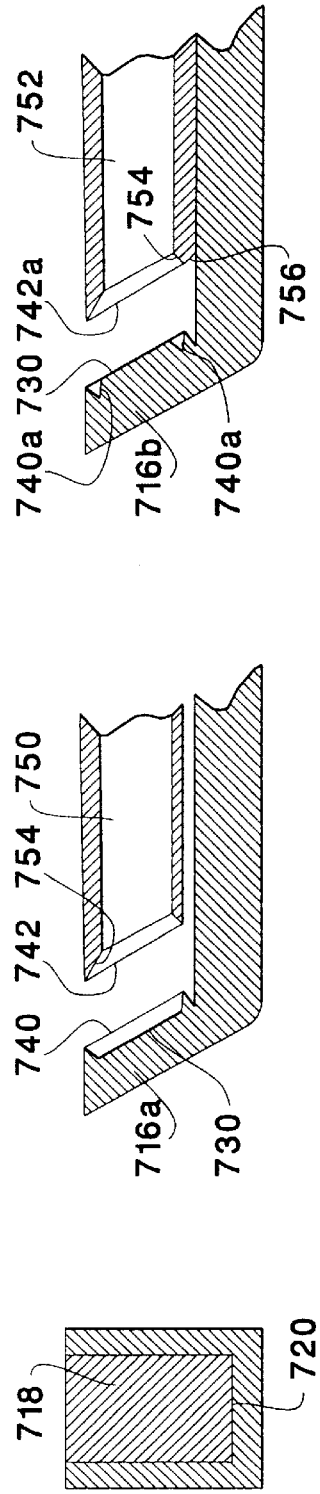
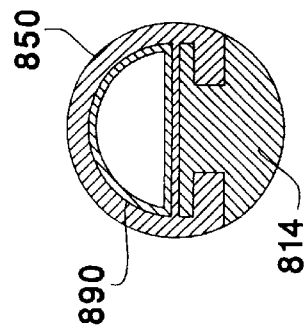
FIG. 27
FIG. 27A
FIG. 27B
FIG. 27C
FIG. 28
FIG. 29

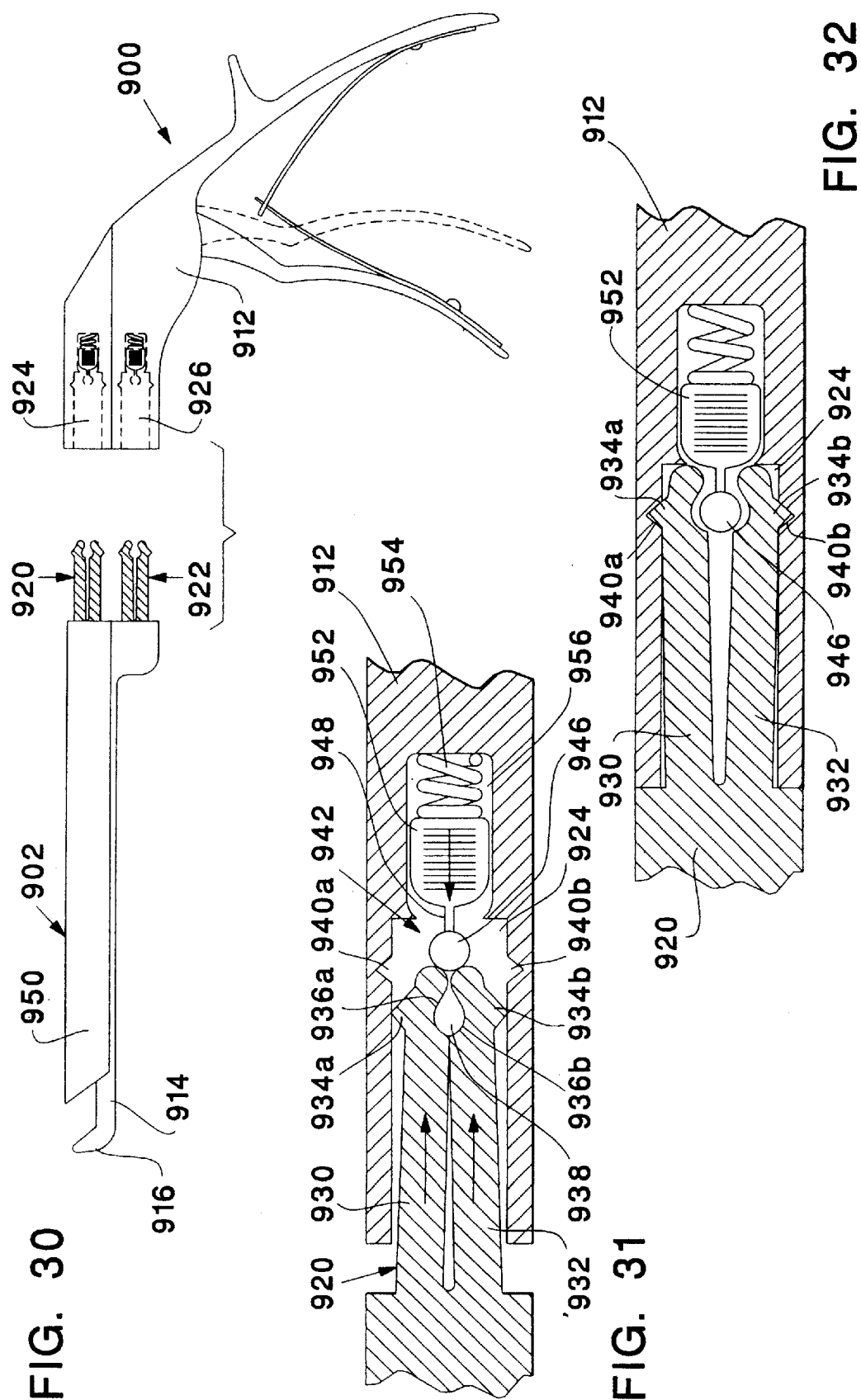

SURGICAL RONGEUR

This application is a division of application Ser. No. 08/337,107 filed on Nov. 10, 1994, now U.S. Pat. No. 5,653,713 which is a continuation in part of application Ser. No. 08/108,908 filed on Aug. 18, 1993 which is a continuation in part of application, Ser. No. 07/905,127, filed on Jun. 24, 1992 abandoned, which is a continuation of application, Ser. No. 07/398,987, filed on Aug. 28, 1989 which is a continuation in part of application, Ser. No. 07/341,849, filed on Apr. 24, 1989, now U.S. Pat. No. 5,009,661.

BACKGROUND OF THE INVENTION

1. Field of the Invention

This invention relates to surgical instruments, used to bite out or cut portions of bone or cartilage, and specifically to those of the Kerrison type, or similar type.

2. Description of the Related Art

Rongeurs are surgical instruments for the cutting away of human tissue, and most commonly, cartilage and/or bone. Kerrison rongeurs are utilized in spinal surgery to remove bone and to thereby gain access to the spinal canal. These rongeurs typically have a closable jaw, one member of which having a cutting end and the other member being a foot plate which must be placed beneath the tissue, generally bone or cartilage, to be cut.

For example, when a Kerrison rongeur is in use, the surgeon places the bone to be cut, such as the leading edge of the lamina of a vertebrae, within the open portion of the distal end of the rongeur. The surgeon then squeezes the handle of the rongeur which causes the moveable jaw member of the rongeur to be advanced through that portion of bone to reach the foot plate, and thereby amputating that portion of bone. Once the jaw members become full, the rongeur must then be completely removed from the surgical site and passed to the scrub nurse for the removal from the instrument of that cut portion of bone.

To facilitate the necessary function of the rongeur, the foot plate is generally cupped, as is the cutting end of the moveable jaw member. If only the moveable jaw member were cupped and the foot plate flat, then upon cutting with such an instrument the bone would be so compacted into that singular cup as to make it nearly impossible to remove the portion of bone cut. However, because the foot plate of the Kerrison rongeur is below the lamina and proximate to the dural sac, spinal cord, and nerve roots, there is a compelling need to avoid any excessive thickness of the foot plate itself. Therefore, the foot plate cup is generally not quite as deep as the cup in the moveable jaw member and thus, even in the double cup design, the cut portion of bone tends to be compacted proximally, making its removal nevertheless difficult. The removal from the instrument of the cut portion of bone often requires that the scrub nurse use a small rigid hook, or toothed forceps, and often further requires that the physician temporarily relinquish the instrument entirely to make such bone removal possible. Once cleaned, the instrument is returned to the surgeon who, in returning it to the surgical site, must then reorient himself to the task at hand. This sequence must then be repeated over and over again with each cut of bone. Typically, such spinal procedures unfortunately require many such cuts.

Essentially flat foot plates had been in use earlier this century, but proved to be undesirable because the opening of the jaw members to be able to get around the thickened portions of the vertebrae tended to exceed the capacity of the cup in the moveable jaw member and the bone cut would be markedly compressed during the cutting process. When the foot plate is flat, the mass of bone bitten is forcefully compacted into the singularly cupped recess of the movable jaw member such that it is extremely difficult to remove that bone after each cut.

A consideration of the structure and function of the prior art rongeurs, and specifically in regard to the foot plate structure and its requisite thickness, is quite revealing. It would appear that in use the foot plate is subjected to five types of forces.

Consistent with its intended purpose, the foot plate is subjected to, and must withstand, that force necessary to actually cut through the bone, which shall be referred to as the Bone Cutting Force. However, the surgeon has no way of knowing what that force is, or even when he has reached or exceeded it. Accordingly, the foot plate is invariably exposed to a second force significantly greater than the Bone Cutting Force which shall be called the Terminal Squeezing Force. The Terminal Squeezing Force occurs after the bone fragment has been cut and is caused by the surgeon generating force in excess of the Bone Cutting Force. This results in the relatively massive slide portion of the instrument being driven with great mechanical advantage against the foot plate. This occurs because the manufacturer of such a rongeur must allow for wear of the cutting surfaces and still allow for the jaw to still be able to close such that the slide portion of the instrument has a greater excursion than would be otherwise required to merely close the jaw members of the rongeur when the cutting surfaces are new.

A third force encountered by the foot plate is a product of the fact that the instrument jaw generally opens to an extent greater than the combined depths of the cups such that the solid bony contents are physically crushed. This is the Bone Crushing Force, and again is additional to the Bone Cutting Force.

A fourth force that may impact upon the foot plate is that which occurs when the jaws of the rongeur encounter an object, which because of its physical structure, is unbiteable. In this situation, while the jaw is still in a relatively open position, again a force greater than the Bone Cutting Force is generated and in this case is then transmitted through the unbiteable object to the foot plate.

The fifth force to which the foot plate is subjected is leverage. When the jaws are not sufficiently sharp, or are worn such that they fail to completely close, then the bone will not be completely cut through, and the surgeon will rock the instrument back and forth to fracture through the remaining bony bridge. In this situation, the angle of the jaw in contact with the leading edge of the lamina becomes the fulcrum point and the foot plate, measuring generally less than half of an inch in length, is one lever arm, while the remainder of the instrument through the shaft and handle is the other. Since these instruments generally measure on the order of approximately 10 inches, the mechanical advantage, or force applied to the tip in a rocking maneuver is on the order of magnitude of 20 to 1.

The ability to safely withstand repeated exposure to these five forces, and the previously discussed need to cup the inner surface of the foot plate, have in the past, determined the requisite thickness of the foot plate.

At present, there is also a need for a rongeur with a capacity to remain within the wound and to repeatedly bite bone and to store the bone bitten until all the requisite bone removal has been completed without the need to continuously remove the rongeur from the wound for the purpose of removing the cut portion of bone from the instrument to clear the cutting edges. A further and related need exists for a rongeur that would collect and contain all of the bitten material such that the delicate neural structures would be protected from contact with the bitten material and/or any cogenerated inadvertent debris. In this regard, any rongeur can bite more than once, but not properly. That is, one could deliberately take several small bites, each of which would fail to fill the cup in the foot plate and the singularly cupped recess of the moveable jaw member, in lieu of taking one full bite. However, once the cup in the foot plate and the cupped recess of the moveable jaw member are filled, further biting is not possible. Bone may be crushed as cups that are already full approach one another, but their contents will shield any further interposed bone from the cutting edges, thus making any further bone cutting impossible.

An example of a multibite rongeur is shown in U.S. Pat. No. 3,902,498 issued to Niederer on Sep. 2, 1975. Niederer teaches the use of a rongeur hollow at the tip such that it is possible to take several bites. Unfortunately, since the hollow tip is open to the wound at both ends, the further use of the instrument pushes the already bitten material out of the other end of the hollow tip and back into the depths of the surgical wound where it can cause great harm. This shortcoming of Niederer can not be overcome by simply closing off the second opening as the operation of the instrument requires the second cutting member (8) to pass through the same area that the ejected bone had occupied.

Further, if a rongeur could take and then store safely, multiple full bites of bone, a rationale would then exist for a power rongeur. A prior art power rongeur was marketed by the 3M Company. However, it was very bulky and required a large bore hose connection to a non-sterile compressed gas tank making the instrument very unwieldy. The biting mechanism itself was rather slow and clumsy and the instrument still required removal from the wound after every bite to clean out the bitten portions of bone.

There is also a need for a disposable cutting means so that those portions of the rongeur involved in the actual cutting may be easily renewed as these portions of the rongeur rapidly wear and dull from the cutting of bone. With wear comes both edge dullness and non-mating of the contact surfaces rendering the rongeur ineffective and even dangerous as it fails to cut cleanly and begins to rely on tearing.

Both U.S. Pat. No. 3,902,498 issued to Niederer and U.S. Pat. No. 5,026,375 issued to Linovitz et al. disclose a means for replacing the cutting element on just one side of the jaw in a rongeur appearing to have cutting cupped portions on both sides of the jaw. Since dulling and wear occurs equally on both sides of the jaw, replacing only one side is obviously ineffective in restoring the sharpness and the full cutting function of the instrument or for even providing for the proper mating of the cutting surfaces as one new side is then opposed to one worn side.

Reference is made to U.S. Pat. No. 4,722,338 to Wright et al. and U.S. Pat. No. 4,777,948 to Wright et al. U.S. Pat. No. 4,777,948 discloses a rongeur having a stationary hollow tubular cutting element 28 which may be removably attached to the rongeur. The entire assembly must be disengaged to replace the cutting element. The device is not capable of taking multiple full bites since only a short recess is provided for pulling the severed bone into the hollow cutting tube and contrary to that concept teaches that the bone is then ejected after each cutting operation, as explained in U.S. Pat. No. 4,722,338 at Col. 3, line 10. No collection of the cut bone is achieved by the hollow cutting element beyond a single cut and the cut bone is then ejected. In fact, the cut bone may be ejected into the wound, which could cause great harm.

Finally, there is a need for a Kerrison type rongeur that is capable of taking larger bites of bone than is now possible. While the need for such a rongeur exists, by prior art technology the foot plate would be too thick to safely use beneath the lamina, and the surgeon would lack the strength to crush and compact that volume of bone.

There is therefore a need for a Kerrison type rongeur with a thin, but strong, foot plate that would be able to take and safely store throughout the operation multiple full bites of bone. Such a rongeur would also have at least a disposable cutting element system capable of replacing all cutting edges to provide for the surfaces of the cutting edges to be sharp and close perfectly and would be capable of taking larger bites of bone than previously possible. Such a rongeur could be powered without the need for external connections to a remote power source.

SUMMARY OF THE INVENTION

The present invention is a rongeur for cutting bone or cartilage comprising two shaft members capable of reciprocating motion relative to each other wherein one shaft member terminates in a foot plate and the other shaft member comprises a combined cutting element and storage member. The combined cutting element and storage member has a cutting edge at its distal end and a storage chamber proximate the cutting edge for collecting and storing cut pieces of bone or cartilage in an amount greater than the maximum bone or cartilage capable of being cut in a single full cut. In one embodiment of the present invention the surgical rongeur is an ultra-thin foot plate, multi-bite (capable of taking multiple full bites) rongeur with a combined cutting element and storage member that is replaceable and disposable. The combined cutting element and storage member comprises a removable and disposable straw member having a sharp cutting end and an end that removably attaches to an engagement means for engaging the straw member to a carriage member such that the end is closed while in use. The combined cutting element and storage member is removably locked to at least one of the two shaft members.

The reciprocating motion of the two shaft members causes the combined cutting element and storage member and a foot plate to close and open in response to the activation of a driving member which may be hand operated or powered by a solenoid. The foot plate of the rongeur of the present invention is ultra-thin, such that it is substantially thinner than the foot plates of the rongeurs of the prior art. The ultra-thin foot plate of the present invention is made possible by the relative absence of any recess sufficient to hold bone after a cut is made and is substantially flat. The foot plate of the present invention need not be as thick as that of a conventional rongeur since the only force normally applied to it is that sufficient to actually cut the bone being bitten.

In one embodiment of the present invention, the foot plate-shaft junction area of the rongeur is designed to prevent the upward excursion of the combined cutting element and storage member along the foot plate. The terminal squeezing force is eliminated by providing a proximal stop to the movement of the slide portion of the instrument allowing only for the full opposition of the foot plate and combined cutting element and storage member but allowing no further motion. This absence of further motion in opposition to the foot plate thus serves to consequently protect it.

The bone compaction force that occurs with prior art rongeurs results from the fact that the rongeur must—to serve its purpose—open to an extent sufficient to accept the thickness of the bone being cut, which commonly exceeds the capacity of the two cupped surfaces. However, the present invention has no fully cupped surfaces and in fact the combined cutting element and storage member is functionally bottomless until full.

The force associated with levering is eliminated by eliminating the need for it which generally arises from a need to complete the cutting out of a piece of bone by fracturing through the remaining portion when such cutting is incomplete because of dulling of the cutting elements or a failure of them to fully and uniformally coapt. In the instance of the present invention as the cutting element is not only replaceable, but disposable, and as there is but a single cutting element which is replaceable for each new procedure the surgeon is assured that all of the cutting surfaces are optimally sharp and unworn such that those biting surfaces coapt perfectly. Prior art rongeurs that replaced but one of two equally important cutting edges failed to either restore full sharpness or to provide for perfect coaptation of those cutting surfaces.

During use, the combined cutting element and storage member is closed at its proximal end and open at its distal end terminating in an ultra-sharp cutting surface. Inasmuch as the combined cutting element and storage member is hollow, rather than cupped, and the opposed surface of the foot plate is substantially flat, the bone bitten is always driven rearward into the storage member portion. As the storage chamber is closed while in use except for the cutting entrance, it may be used to repeatedly bite bone without the danger of the bone bitten coming free and falling into the spinal canal in contradistinction to prior art rongeurs which required the ejection of bone before a second full bite could be taken.

When the present invention has completed its task and has removed all of the bone as needed, the combined cutting element and storage member may be removed from the shaft of the rongeur and the bitten bone may be removed from the storage member and made available for use, as in performing a spinal fusion.

The present invention allows for the clean cutting of bone or cartilage without any significant compaction. Further, as the combined cutting element and storage member of the present invention is disposable and thus always fresh and sharp, less force is required during the actual cutting of the bone. In addition, since the combined cutting element and storage member is always fresh and sharp, edge wear is not a problem and the capacity for further excursion of the combined cutting element and storage member towards the foot plate is unnecessary and may be completely blocked, thereby sparing damage to the foot plate.

Further, the present invention has a combined cutting element and storage member that is truly disposable, rather than merely replaceable and requires no special assembly or the use of any tools. The combined cutting element and storage member is simply placed onto one of the shaft members whereby it is immediately locked into place by the use of the instrument itself.

Finally, as the rongeur of the present invention is capable of taking repeated and uninterrupted multiple full bites of bone or cartilage, there is a compelling rationale for the incorporation of a power means to drive the rongeur and a self-contained power source to further allow the use of the rongeur to be unfettered.

OBJECTS OF THE PRESENT INVENTION

It is an object of the present invention to provide an improved surgical rongeur capable of taking multiple full bites of bone or cartilage without having to be removed from the wound after each bite.

It is another object of the present invention to provide an improved surgical rongeur capable of storing multiple cut pieces of bone or cartilage while the rongeur is in the wound.

It is yet another object of the present invention to provide an improved surgical rongeur having a combined cutting element and storage member.

It is a further object of the present invention to provide an improved surgical rongeur having a combined cutting element and storage member that is easily replaceable and disposable.

It is yet a further object of the present invention to provide an improved surgical rongeur having a replaceable and disposable combined cutting element and storage member that does not require the use of tools or special assembly.

It is still a further object of the present invention to provide an improved surgical rongeur having a combined cutting element and storage member which is simply placed onto the shaft of the rongeur, whereby it is immediately locked into place by the use of the rongeur.

It is another object of the present invention to provide an improved surgical rongeur with an ultra-thin foot plate.

It is a further object of the present invention to provide an improved surgical rongeur having an improved button assembly for controlling the displacement of a driving means along the shaft of the rongeur and for controlling the engagement or release of a combined cutting element and storage member, that also functions as a hinge for attaching the handle to the body of the rongeur.

It is another object of the present invention to provide an improved surgical rongeur having an improved means for the rapid engagement and disengagement of a disposable combined cutting element and storage member.

It is yet another object of the present invention to provide a surgical rongeur capable of taking multiple full bites which is activated by a solenoid.

It is still another object of the present invention to provide an electrical rongeur having a battery as a self-contained power source.

It is another object of the present invention to provide a surgical rongeur having a removable shaft portion which can be made in a variety of sizes and configurations and be interchangeably coupled to a manual or power handle means, wherein at least a portion of the removable shaft portion may be disposable.

It is still another object of the present invention to provide a surgical rongeur having a combined cutting element and storage member in communication with a vacuum means for evacuating any contents of the combined cutting element and storage member.

These and other objectives of the present invention shall be more clear upon review of the following detailed description of the drawings when reviewed in conjunction with the accompanying drawings.

BRIEF DESCRIPTION OF THE DRAWINGS

FIG. 2 is an exploded first side view of the surgical rongeur of FIG. 1.

FIG. 4 is an exploded view of the surgical rongeur of FIG. 1 showing a bottom plan view of the slide drive member engaged to the cutting/storage member and an elevational second side view of the body.

FIG. 5 is a top plan view along lines 5—5 of FIG. 4 showing the configuration of the slot and recess of the shaft portion of the surgical rongeur of FIG. 1.

FIG. 6 is a cross sectional view along lines 6—6 of FIG. 1 illustrating the cutting/storage member engaged to the shaft of the surgical rongeur of FIG. 1.

FIG. 7 is a partial schematic view of the spring means for biasing the handle of the surgical rongeur of FIG. 1.

FIG. 27 is a top plan view along lines 5—5 of FIG. 4 showing an alternative embodiment of the surgical rongeur of the present invention having a shaft with a removably attachable end portion.

FIG. 27A is a cross sectional view along lines 27A—27A of FIG. 27 showing the engaging means for removably engaging the end portion to the shaft of the surgical rongeur of FIG. 27.

FIG. 27B is a partial side sectional view of an alternative embodiment of the foot plate having a cutting surface which is out of the plane of the surface of the foot plate facing the cutting edge of the cutting/storage member of the present invention.

FIG. 27C is a partial side sectional view of an alternative embodiment of the foot plate having a cutting surface which is out of the plane of the surface of the foot plate facing the cutting edge of the cutting/storage member of the present invention.

FIG. 28 is a partial elevational side view of an alternative embodiment of the surgical rongeur of the present invention for use in endoscopic surgical procedures.

FIG. 29 is a cross sectional view along lines 29—29 of the endoscopic surgical rongeur of FIG. 28.

FIG. 30 is an exploded elevational side view of an alternative embodiment of the surgical rongeur of the present invention having removably attachable shaft members.

FIG. 31 is a cross sectional view of the engagement means for engaging the removably attachable shaft members of the surgical rongeur of FIG. 30 shown partially inserted.

FIG. 32 is a cross sectional view of the engagement means for engaging the removably attachable shaft members of the surgical rongeur of FIG. 30 shown fully inserted.

DETAILED DESCRIPTION OF THE DRAWINGS

Figure 1:
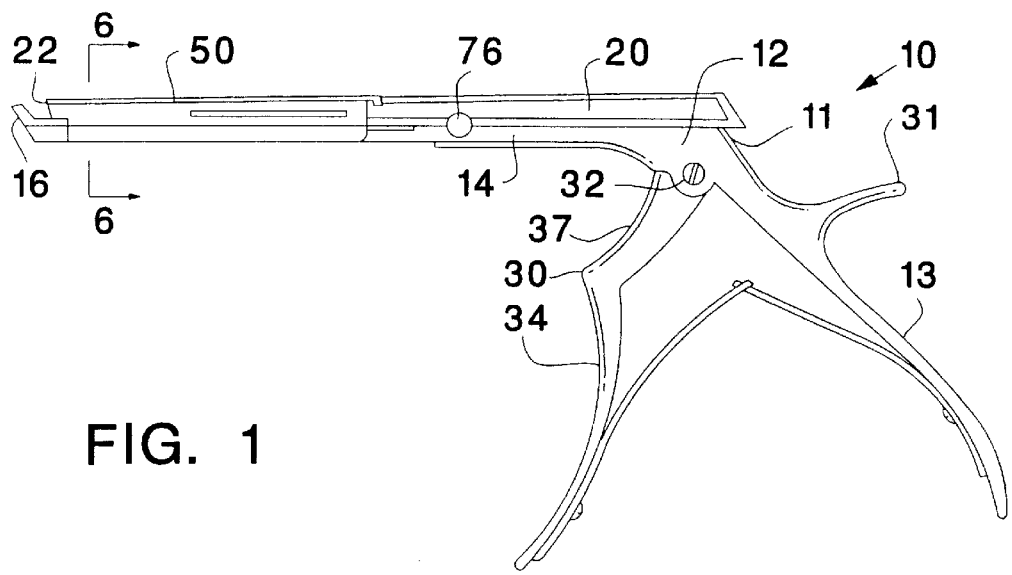
FIG. 1 is an elevational side view of a surgical rongeur constructed in accordance with the present invention.
Figure 3:
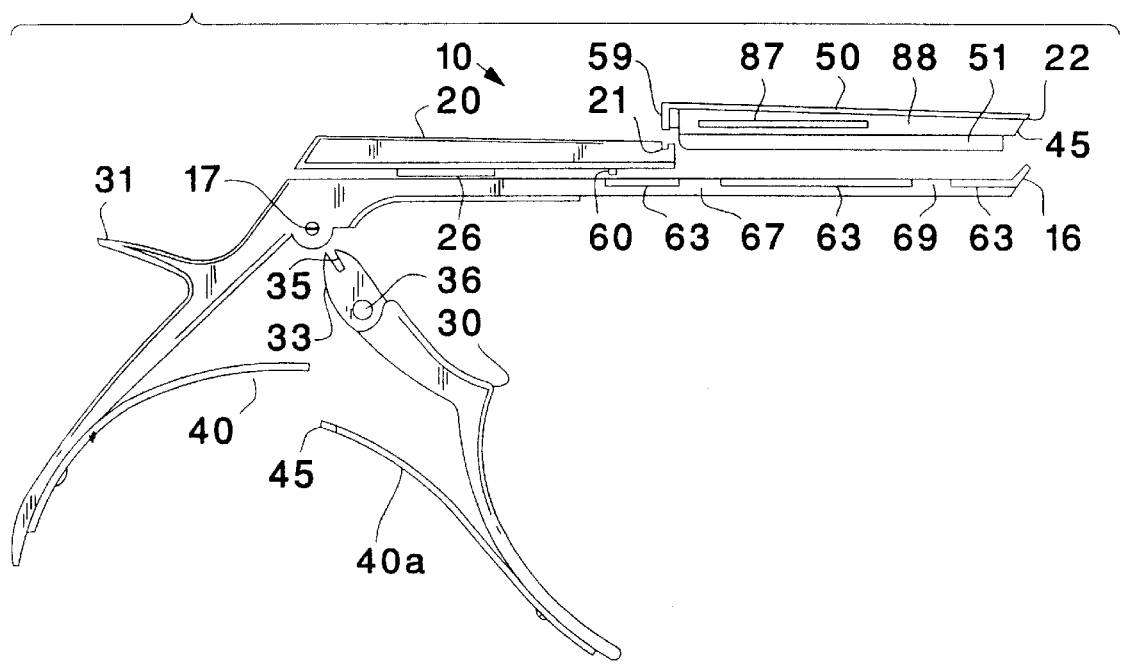
FIG. 3 is an exploded second side view of the surgical rongeur of FIG. 1.

Referring to FIGS. 1–4, the improved surgical bone rongeur 10 is shown constructed in accordance with the present invention and comprises generally of a body 12 having a rear handle 13 depending at an angle from the proximal end 11 of the body 12, and has a shaft 14 extending distally and terminating at its distal end in a foot plate 16. A support spike 31 extends from the upper portion of the rear handle 13 as support for the area of the hand between the thumb and the first finger. Mounted on the shaft 14 is a slide drive member 20 for reciprocating movement on the shaft 14.

Referring to FIG. 2, a pivoting forward handle 30 includes a lower finger grip portion 34 and an upper finger portion 37 for the fingers. The upper part of the forward handle 30 has an extension 33 with an elongated opening 35 and an aperture 36 through which passes a pivot pin 32. Extension 33 fits into the body 12 through slot 19 (shown in FIG. 5) and is contained within the body 12.

Once the extension 33 is positioned within slot 19, the pivot pin 32, having a screw head 39 on one end and threads at its other end, is used to pivotally attach the forward handle 30 to the body 12. The pivot pin 32 passes through opening 15 in one side of the body 12 through aperture 36 in the forward handle 30 and threads into threaded aperture 17 in the other side of the body 12. The elongated opening 35 of the extension 33 surrounds pin 42 located at the bottom surface of slide drive member 20 which is mounted on the shaft 14 so that the forward handle 30 engages the pin 42 and serves as the driving means for the slide drive member 20. The forward handle 30 is attached to the body 12 at an angle to the slide drive member 20 so that when the forward handle 30 moves proximally the slide drive member 20 moves distally. The forward handle 30 and the rear handle 13 are biased away from each other by spring means 40 and 40a. Spring means 40 is attached at one end to the bottom of forward handle 30 by screw 41 and spring means 40a has one end attached to the bottom of rear handle 13 by screw 43 and may be further secured by having a bend in the end of spring means 40a capable of fitting into an opening of rear handle 13 to prevent rotation of the spring means 40a relative to rear handle 13.

Referring to FIG. 7, in order to interlock the two spring means 40 and 40a, spring means 40 has an extension piece 45 at its upper end that fits into the notch 46 of the upper end of spring means 40a. Once interlocked, the spring means 40 and 40a oppose each other to bias the forward handle 30 distally. Other spring mechanisms, internal or external, and other biasing means, including pneumatic means, may also be employed for urging the forward handle 30 distally.

Referring to FIGS. 4 and 5, the slide drive member 20 is slidably mounted to the top surface of shaft 14 within a slot 24 formed in the shaft 14 having an inverted T-shaped portion 25 into which is fitted a complementary inverted T-shaped runner 26 depending from the bottom surface of slide drive member 20. Slot 24 extends distally from the inverted T-shaped portion 25 to form a wider portion 27 of the slot 24.

Referring to FIG. 4, a stop pin 60 depends from the distal end 61 of the bottom surface of the slide drive member 20. The stop pin 60 serves to guide the slide drive member 20 and to keep the distal end 61 of the slide drive member 20 from sliding off the shaft 14 during the operation of the rongeur 10. The stop pin 60 is set back from the distal end 61 of the slide drive member 20 and fits within the wider portion 27 of slot 24. The wider portion 27 of the slot 24 has a slot wall 28 at its distal end which catches the stop pin 60 and prevents the slide drive member 20 from sliding off the shaft 14 distally.

Referring to FIGS. 2 and 5, on one side of the shaft 14 is a rounded aperture 80. The rounded aperture 80 corresponds in location to a recess 82 in the top surface of shaft 14 as shown in FIG. 5. The recess 82 bisects the wider portion 27 of slot 24 and has a rounded bottom surface. Located within the recess 82 and extending from the aperture 80 is a push button assembly 70 having a large diameter, external button portion 76 and a narrow diameter portion 74 that passes through the aperture 80. The narrow diameter portion 74 has a depression 75 with a flat bottom. The narrow diameter portion 74 terminates at its other end in a large diameter member 72 having a slightly smaller diameter than the diameter of the rounded recess 82. The large diameter member 72 has a flattened top surface 73 so that it is flush with the top surface of the shaft 14 when the large diameter member 72 is inserted within the recess 82. The reverse end of the large diameter member 72 has a small depression 77 for receiving the end of a coil spring 84 a shown in FIG. 4.

The large diameter member 72 is placed within the recess 82, so that the narrow diameter portion 74 crosses the wider portion 27 of the slot 24 at a right angle and extends through the rounded aperture 80 and the external button portion 76 is external to the shaft 14. The depression 75 in the narrow diameter portion 74 is of a sufficient depth to permit the stop pin 60 depending from the slide drive member 20 to easily pass through the wider portion 27 of the slot 24 and over the depression 75 unobstructed by the narrow diameter portion 74.

Within the recess 82 is a coil spring 84 having an end that fits within the small depression 77 of the large diameter member 72. The coil spring 84 serves to bias the large diameter member 72 so that in its biased position, the large diameter member 72 blocks the wider portion 27 of slot 24. The large diameter member 72 has a diameter that is sufficient to prevent the stop pin 60 from sliding over it. The external button portion 76 is at its greatest extension out of the rounded opening 80 when the large diameter member 72 is in the biased position and blocks the wider portion 27 of the slot 24. To unblock the wider portion 27 of the slot 24, the user simply presses the external button portion 76 of the button assembly 70 so that the coil spring 84 compresses and the large diameter member 72 moves further into the recess 82. When the large diameter member 72 is positioned as far into the recess 82 as possible the depression 75 of the button assembly 70 is positioned directly beneath the stop pin 60 depending from the bottom surface of the slide drive member 20 so that the stop pin 60 can pass through the wider portion 27 of the slot 24 unobstructed.

Figure 17:
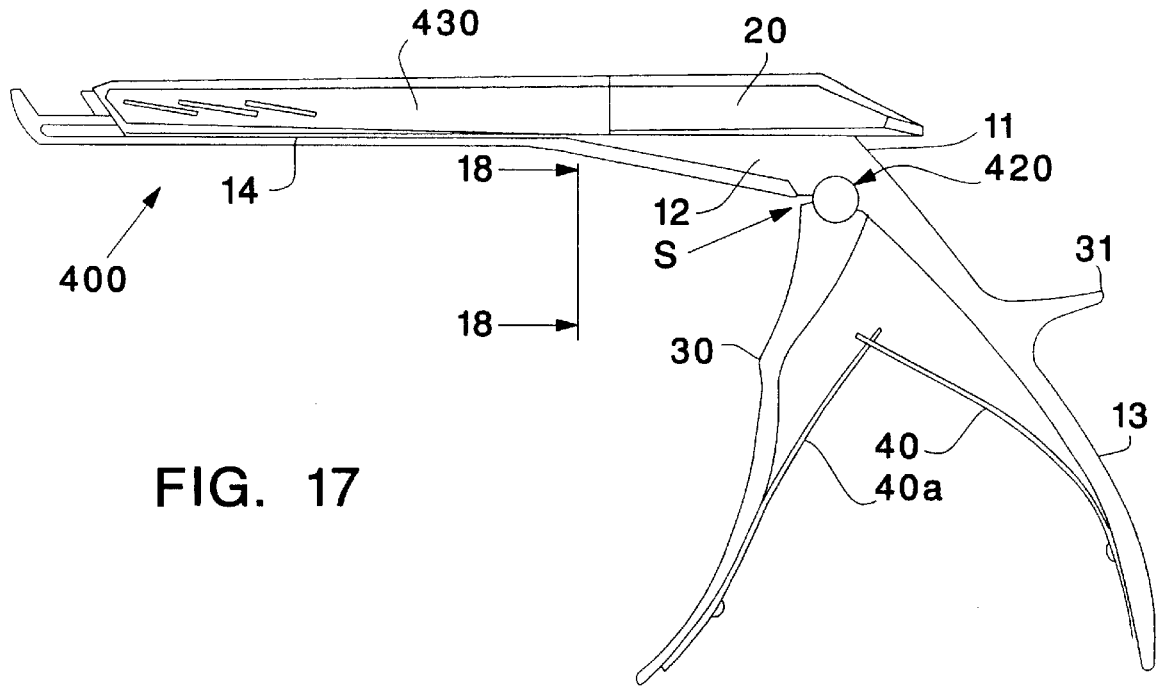
FIG. 17 is an elevational side view of an alternative embodiment of the surgical rongeur of the present invention.

It is appreciated that the rounded recess 82 may be placed at various locations along the shaft 14 so that the button assembly 70 contained therein may also be positioned at various locations along the shaft 14 beneath the slide drive member 20. The position of the stop pin 60 depending from the slide drive member 20 may also be changed to correspond to the location of the button assembly 70 and the configuration of the slot 24 and the position of the wider portion 27 may also be modified accordingly without departing from the scope of the present invention. For example, the rounded recess 82 may be replaced along the shaft 14 so that it is located within the opening 15 and the threaded aperture 17 of the body 12. In this position, the button assembly 70 in addition to controlling the displacement of the slide drive member 20 along the shaft 14 could also serve as a hinge and attachment means for the forward handle 30 replacing the pivot pin 32 as shown in FIG. 17.

Referring to FIGS. 5 and 6, the shaft 14 has a pair of rails 62,63 extending from either side of the shaft 14 which run parallel to the shaft 14. The rails 62,63 have a bottom substantially flat surface 64 that is perpendicular to the sides of the shaft 14 as shown in FIG. 6. Near the distal end of the shaft 14 are forward notches 65,66 that provide a break in the continuity of the rails 62,63. Positioned proximal to the forward notches 65,66 are rear notches 69,71 which similarly provide a break in the continuity of the rails 62,63.

Referring to FIGS. 4 and 6, the distal end 61 of the slide drive member 20 engages a cutting/storage member 50 which is removably attached to both the shaft 14 and to the slide drive member 20. The cutting/storage member 50 has depending sides 51 and 52 which are mirror images of each other. As shown in FIG. 4, near the distal end of the cutting/storage member 50, the depending sides 51,52 each have forward rail-engaging members 53,54 respectively. Forward rail-engaging members 53,54 fit within the forward notches 65,66 of shaft 14. Each of the forward rail-engaging members 53,54 has a top substantially flat surface 68 that is perpendicular to the depending sides 51 and 52 for engaging the bottom substantially flat surface 64 of rails 62,63 as shown in FIG. 6. Once the forward rail-engaging members 53,54 are engaged to the rails 62,63, the cutting/storage member 50 is prevented from sliding upward as it moves along the shaft 14.

Also located on each of the depending sides 51,52 of the cutting/storage member 50 are rear rail-engaging members 56,57 which are sufficiently spaced proximally from the forward rail-engaging members 53,54 so that when the forward rail-engaging members 53,54 are placed over forward notches 65,66, the rear rail-engaging members 56,57 are directly over the rear notches 69,71 in the shaft 14. The rear rail-engaging members 56,57 are identical to the forward rail engaging members 53,54 and similarly each have a top substantially flat surface 68 for engaging the bottom substantially flat surface 64 of rails 62,63.

Referring to FIGS. 2 and 4, the proximal end of the cutting/storage member 50 has a male connection means 55 having grooves 58 on both sides of a key portion 59. The male connection means 55 fits into a female connection means 21 located at the distal end 61 of the slide drive member 20. The female connection means 21 has rails 23 for engaging the grooves 58 of the male connection means 55 and a notched area 78 for receiving the key portion 59. The cutting/storage member 50 may be engaged to the slide drive member 20 by lowering the cutting/storage member 50 toward the slide drive member 20 so that the male and female connection means 55 and 21 slide into each other. To disengage the cutting/storage member 50 from the slide drive member 20, the cutting storage member 50 is simply lifted out. As an alternative, the cutting/storage member 50 may also be attached to the slide drive member 20 in any number of conventional ways, such as by snap fit.

The cutting/storage member 50 is placed on the shaft 14 by aligning the forward rail-engaging members 53,54 with the forward notches 65,66 and by simultaneously aligning the rear rail-engaging members 56,57 with the rear notches 69,71 so that the male connection means 55 slides into and engages the female connection means 21 of the slide drive member 20. In order to properly align the cutting/storage member 50 so that it may engage the shaft 14, the slide drive member 20 must be positioned sufficiently proximal from the foot plate 16.

The range of proximal to distal movement of the slide drive member 20 is controlled by the large diameter member 72 of the button assembly 70. In its biased position, the large diameter member 72 is positioned in the wide portion 27 of slot 24 is that the distal edge 79 of the large diameter member 72 blocks the stop pin 60 and thus the slide drive member 20 from moving proximally along shaft 14. The appropriate position of the slide drive member 20 for attaching the cutting/storage member 50 to the shaft 14 may only be achieved by sliding the stop pin 60 past the position of the distal edge 79 of the large diameter member 72. In order to slide the stop pin 60 past the distal edge 79, the button assembly 70 must be manually depressed toward the shaft 14 so that the large diameter member 72 is pushed into the recess 82 and is moved out of the wide portion 27 of slot 24. As the forward handle 30 is biased forward by the spring means 40 and 40a, the slide drive member 20 is moved proximately along the shaft 14 so that the stop pin 60 is positioned within the depression 75 of the narrow diameter portion 74. With the stop pin 60 positioned within the depression 75, the large diameter member 72 is pushed back within the recess and the coil spring 84 is compressed within the recess 82 of the shaft 14.

Once aligned with the forward and rear notches 65,66 and 69,71 and engaged to the slide drive member 20, the cutting/storage member 50 is in position to be pushed distally along shaft 14 by the slide drive member 20 toward the foot plate 16. This is accomplished by squeezing the forward handle 30 to move the slide drive member 20 and the stop pin 60 distally so that the stop pin 60 is no longer within the depression 75 of the narrow diameter portion 74, and the large diameter member 72 is returned to its biased position by the coil spring 84. As the cutting/storage member 50 is engaged to the slide drive member 20, the movement of the cutting/storage member 50 is responsive to the movement of the slide drive member 20. As the cutting storage member 50 is moved distally the front and rear rail-engaging members 53,54 and 56,57 engage the rails 62,63.

Once the cutting/storage member 50 engages the rails 62,63 of the shaft 14, it may not be lifted out and the cutting/storage member 50 is locked to the shaft 14. The proximal movement of the slide drive member 20 is stopped by the large diameter member 72 in its biased position which blocks the stop pin 60 from further proximal travel in the wider portion 27 of the slot 24. To remove the cutting/ storage member 50 from the shaft 14, the stop pin 60 must be again positioned by the user so that it is within the depression 75 of the narrow diameter portion 74. Thus, the cutting/storage member 50 may be locked or unlocked to the shaft 14 without the use of tools by simply pressing the button assembly 70. Further, once the button assembly 70 is pushed and the forward handle 34 is advanced by the handle biasing means 40 and 40a, the rongeur 10 remains receptive to the introductions or removal of the cutting/storage member 50 without the need to continue depressing the release button.

Further, the cutting/storage member 50 is secured to the shaft 14 by simply pulling the forward handle 34 securing the cutting/storage member 50 to the shaft 14 until the release button assembly 70 is again depressed. The button assembly 70 does not have to be redepressed to allow pin 60 to move distally as portion 75 is of sufficient length to support it when the slide drive member 20 is maximally proximal.

The cutting/storage member 50 opens into a storage chamber 88 which is bounded by upper and side walls 44 and 85 which are sharpened distally to form cutting edges 22 facing the foot plate 16. The depending sides 51,52 of cutting/storage member 50 are recessed from the foot plate 16 for maximum bite since no cutting edge is required at the depending sides 51,52. While the foot plate 16 may have a slight concave depression to allow for a cutting edge, it is to be understood that it is preferably substantially flat, without a cutting edge.

The storage chamber 88 extends along the interior of the cutting/storage member 50 at least partially toward its proximal end. The cross sectional area of the interior of the storage chamber 88 may be constant or may progressively increase from the distal end to the proximal end so that a number of successive bone fragments can more easily slide into the storage chamber 88 and stack up without jamming.

The rongeur 10 of the present invention is used in the conventional manner to bite bone or cartilage. The cut bone fragments are pushed by the foot plate 16, one by one, into a stack within the storage chamber 88 of the removable cutting/storage member 50 after being cut and are not likely to fall back into the wound site because they are forced into the storage chamber 88 with considerable force and are prevented from jamming as the cross sectional area of the interior space of the storage chamber 88 either has parallel or divergent walls. Thus, it is not necessary that the cut bone fragments be removed during the surgical procedure, and bite after bite takes place, without the need to remove the rongeur 10 from the wound.

The side walls 44 and 85 of the cutting/storage member 50 have narrow slits 86,87 partially along the length of the cutting/storage member 50. Once the cutting/storage member 50 is filled with cut pieces of bone, it is removed from the shaft 14 and a stylet or similar instrument may be inserted through the slits 86,87 to aid in the removal of the cut pieces from the storage chamber 88 containing the cut pieces.

Alternatively, the proximal end of the storage chamber 88 of the cutting/storage element 50 may also be open. During use, the distal end 61 of the slide drive member 20 may be used to block the open proximal end of the storage chamber 88. Once the cutting/storage member 50 is removed from the rongeur 10, the proximal end of the storage chamber 88 is open and a stylet may be used to push the cut bone fragments stored within the storage chamber 88 so that the fragments exit from the distal end or in reverse from the proximal end.

The use of a removable hollow cutting/storage member 50 permits a new sharp cutting edge to be provided for each operation as it may easily be replaced. Both the storage chamber 88 and the cutting edge 22 could be made of metal or any other suitable material such as, but not limited to, ceramic for the cutting edge 22 or a plastic (e.g. polycarbonate) for the storage chamber 88.

In the preferred embodiment, the rongeur 10 has a body 12 that is approximately 7¼ inches in length; a cutting/storage member 50 that is approximately 3¼ inches in length and approximately ⅞ inches in height and approximately ⅜ inches in width; a slide drive member 20 that is approximately 3 9/16 inches in length and approximately 7/16 inches in height and approximately ⅜ inches in width; a rear handle 13 approximately 4⅞ inches in length and a front handle 30 approximately 4⅜ inches in length having a extension member 33 that is approximately ⅞ inches long; and a button assembly 70 having an overall length of approximately 7/16 inches.

It is appreciated that the cutting elements of the rongeur of the present invention need to be made of a material capable of forming a sharp cutting edge and serving the intended purpose of the rongeur. Such materials include, but are not limited to, metals, ceramics or composite materials. The remainder of the rongeur could be made of metal, plastic or a composite material suitable for the intended purpose, such that the entire rongeur could be disposable.

Figure 8:
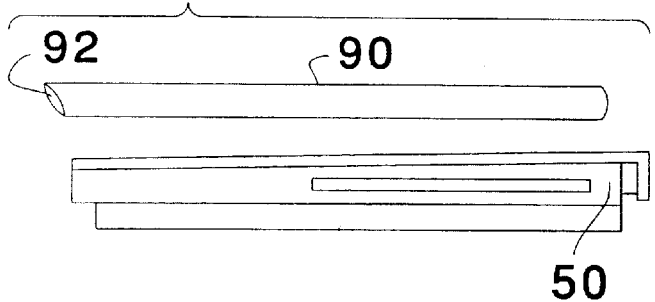
FIG. 8 is a perspective view of an alternative embodiment of the cutting/storage member of the surgical rongeur of the present invention comprising a disposable storage and cutting element.
Figure 9:
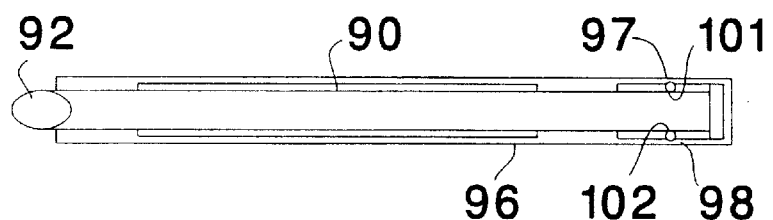
FIGS. 9 is a bottom plan view of a further alternative embodiment of the surgical rongeur of the present invention comprising a disposable combined cutting element and storage member secured to the bottom portion of a carriage member.

Referring to FIGS. 8 and 9, in a first alternative embodiment of the present invention, the rongeur 10 includes a removable and disposable straw 90 that is attachable to the bottom of a carriage member 96. The carriage member 96 is similar in construction to the cutting/storage member 50 but does not have the storage chamber 88 and essentially acts as a housing for carrying the straw 90. Straw 90 is a hollow member in the shape of a cylinder or may have any other shape suitable for use with rongeur 10. At the distal end of the straw 90 is a sharp cutting edge 92 for cutting bone or other similar tissue. In this embodiment, the cutting/storage member 50 is actually a carrier member as the straw 90 does the actual cutting and storing of the bone. Prior to use, the straw 90 is inserted within the storage chamber 88 before the cutting/storage member 50 is placed on the shaft 14. The hollow chamber 94 of the straw 90 functions to store the cut pieces of bone or cartilage. The stored cut pieces may be removed for future use in the same manner described above for the preferred embodiment.

The straw 90 is placed in the bottom of the carriage member 96 prior to placing the carriage member 96 on the shaft 14. The straw 90 is held in place and is prevented from rotating by pins 97,98 which complement the grooves 101, 102 in the straw 90 as shown in FIG. 9, and prevent any movement of the straw 90 within the carriage member 96 during the operation of the rongeur. Once the carriage member 96 is removed from the shaft 14, the straw 90 is easily removable from the carriage member 96.

The straw 90 is preferably made of metal or any other material which is capable of being sharpened and maintaining a sharp cutting edge 92 for multiple bites by the rongeur 10. After the straw 90 is used and removed from the rongeur 10, the cut pieces contained therein are removed and may be used for bone grafting purposes if desired. The relatively low cost of the straw 90 allows the straw 90 to be truly disposable.

Figure 10A:
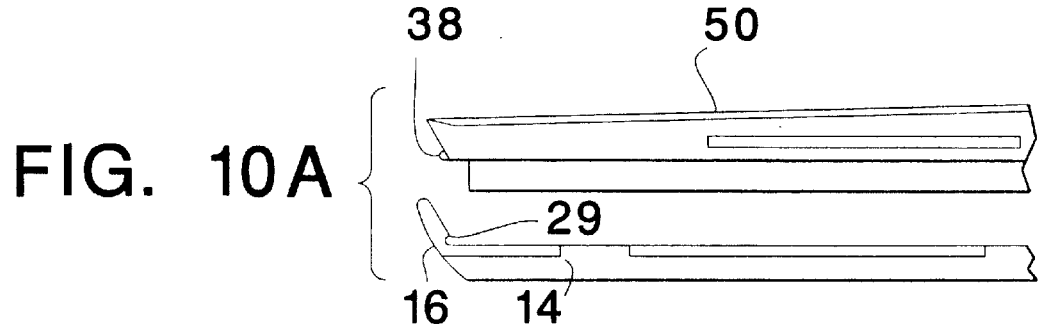
FIGS. 10A and 10B are partial elevational side views of alternative embodiments of the foot plate having a groove and the cutting/storage member having an extension element for preventing upward excursion of the cutting/storage member along the foot plate.
Figure 10B:
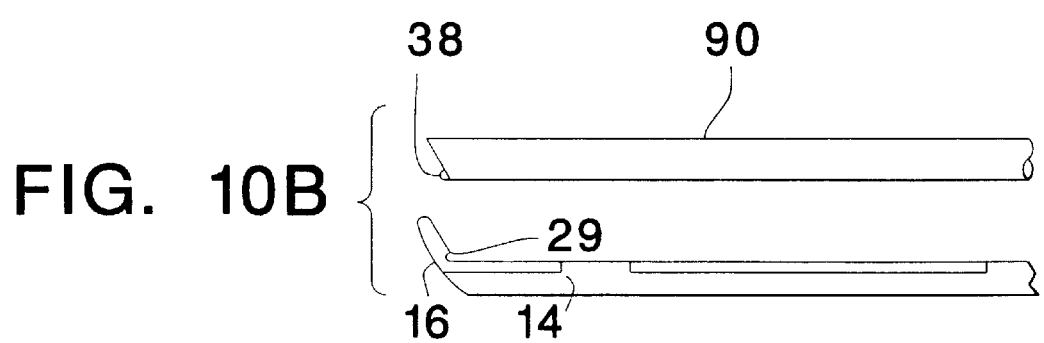

Referring to FIG. 10A and 10B, a second alternative embodiment of the rongeur 10 is shown with the intersection of the foot plate 16 and the shaft 14 having a groove 29 such that the distal end of the cutting/storage member 50 or of a straw 90 has an extension element 38 that complements the shape of the groove 29 and fits within the groove 29. The extension element 38 may be made of the same material as the cutting/storage member 50. As a result of the angled orientation of the foot plate 16, when the rongeur is fully closed, the cutting/storage member 50 or the straw 90 tends to be forced up the inclination of the foot plate 16 which may result in damage to the cutting edge 22 or 92. The combination of the groove 29 and the extension element 38 functions to prevent any upward excursion of the cutting/storage member 50 or straw 90 which would result in an overbite.

The operation of the rongeur 10 of the present invention is as follows:

The rongeur 10 is set in the "release position" by positioning the stop pin 60 within the depression 75 of the narrow diameter portion 74 of the button assembly 70. This is accomplished by manually pressing the external button portion 76 of the button assembly 70 so that the large diameter member 72 moves out of the wider portion 27 of the slot 24 to compress the coil spring 84. The stop pin 60 may now freely pass by the position of the distal edge 79 of the large diameter member 72 and to fit within the depression 75. As the spring means 40 and 40a bias the forward handle 30 distally, the slide drive member 20 moves toward the foot plate 16. With the stop pin 60 positioned within the depression 75, the coil spring 84 is kept compressed within the recess 82.

In the release position, the slide drive member 20 is positioned so that the cutting/storage member 50 may be easily placed on the shaft 14. In the release position, the forward rail-engaging members 53,54 are aligned with the forward notches 65,66 and the rear rail-engaging members 56,57 are aligned with the rear notches 69,71. Once aligned, the cutting/storage member 50 is positioned to easily engage the slide drive member 20 so that the male and female connector means 55 and 21 mate and the cutting/storage member 50 rests upon the shaft 14.

Once the cutting/storage member 50 is engaged to the slide drive member 20, the forward handle 30 is squeezed by the user to advance the slide drive member 20 so that the stop pin 60 exits from within the depression 75 and the large diameter member 72 is returned by the coil spring 84 to its biased position to block the wider portion 27 of the slot 24. With the large diameter member 72 in this position, the stop pin 60 is stopped from any further proximal movement past the distal edge 79 of the large diameter member 72 thereby preventing any further proximal movement of the slide drive member 20 past the large diameter member 72. With the slide drive member 20 in this position, the forward and rear rail engaging members 53,54 and 56,57 are engaged to the rails 62,63 and are no longer aligned with the forward and rear notches 65,66 and 69,71. Therefore, the cutting/storage member 50 is securely locked to the shaft 14 and may not be removed from the shaft 14.

With the cutting/storage member 50 in the locked position on the shaft 14, the rongeur 10 may be placed in the wound and used to take multiple bites or cuts of the selected tissue with the cut pieces being stored within the storage chamber 88 of the cutting/storage member 50. Once the desired number of bites has been attained or if the storage chamber 88 becomes filled, the rongeur 10 is removed from the wound. The cutting/storage member 50 is removed from the shaft 14 of the rongeur by returning the rongeur to the release position by pressing the external button portion 76 as described above, so that the forward and rear rail-engaging members 52,54 and 56,57 are once again aligned with the forward and rear notches 65,66 and 69,71 and no longer engage the rails 62,63. The cutting/storage member 50 is then easily lifted up and away from the shaft 14.

The cut pieces may be removed from the storage chamber 88 by inserting a stylet in the slits 86,87 in the side walls 44,45 of the cutting/storage member 50 and pushing the cut pieces out from the chamber. If an alternative embodiment of the cutting/storage element 50 is used where the proximal end of the storage chamber 88 is closed only during use, the cut pieces may be pushed out of either end of the storage chamber 88. Similarly, if a disposable straw 90 is used, the cut pieces contained within the straw 90 may be removed by using a stylet to the push the cut pieces out of either the proximal or the distal end of the straw 90 which are both open when not in use.

Further, the improved surgical rongeur of the present invention may be powered by alternative power sources such as electricity, via a cord or battery supply, pneumatic power, or other power sources can be employed. In a powered rongeur, the finger grip of the rongeur can then be devoted to turning on and off the power supply source to drive the instrument. If gas or other fluid is used, a pressure relief valve is preferably incorporated within the fluid line to establish a limit pressure, which may be set to the maximum desired biting force to be delivered.

Figure 11:
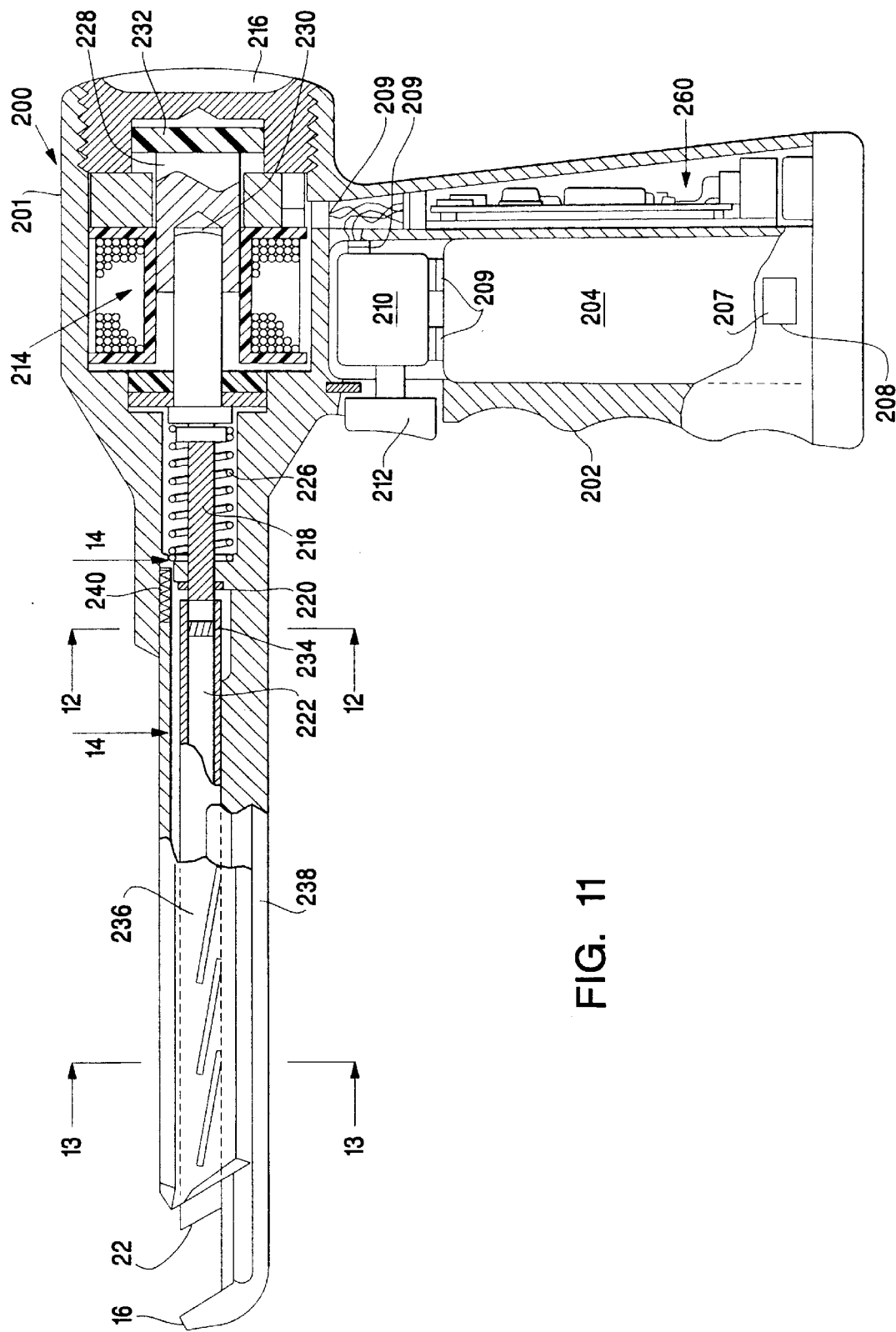
FIG. 11 an elevational and partial sectional side view of an electrically powered surgical rongeur of the present invention.
Figure 12:
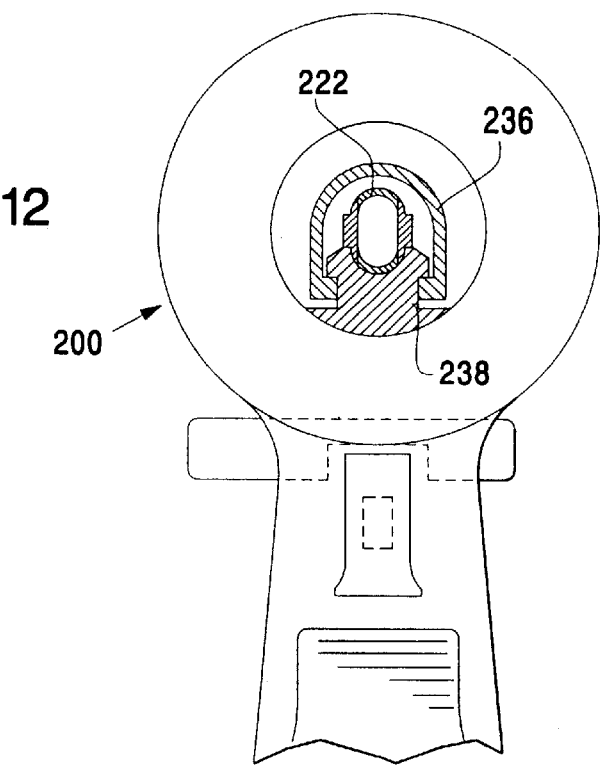
FIG. 12 is a cross sectional view along lines 12—12 of the electrically powered surgical rongeur of FIG. 11.
Figure 13:
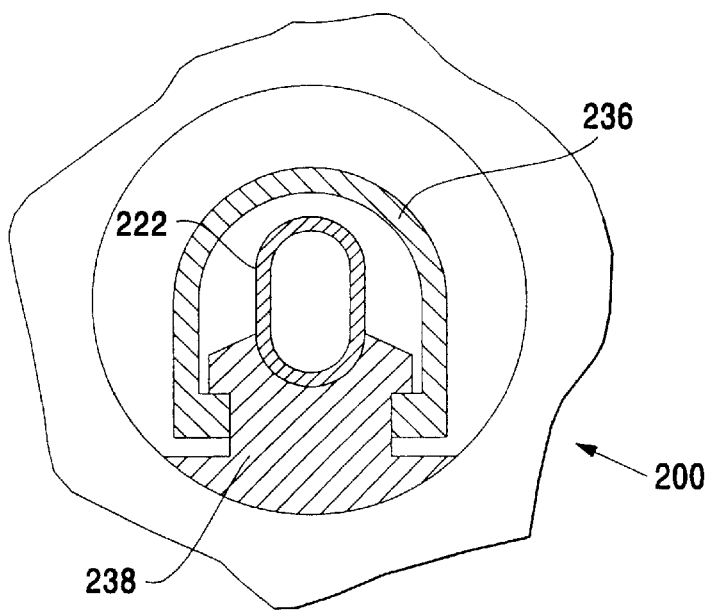
FIG. 13 is a cross sectional view along lines 13—13 of the electrically powered surgical rongeur of FIG. 11.

Referring to FIG. 11, an electrically powered rongeur 200 is shown. The rongeur 200 comprises a housing 201 having a grip 202 that is adapted for receiving a rechargeable battery pack 204 and related electronic circuitry 206. The battery pack 204 is removably inserted into the grip 202 through an opening at the base of the grip 202 and has spring clips 207 on either side of the battery pack 204 which fit into corresponding openings 208 in the grip 202 and lock into place. The battery pack 204 is removed by depressing the spring clips 207 so that they are out of the openings 208 and the battery pack 204 is easily removed from within the grip 202. It is appreciated that in a simple variation of this embodiment, the battery pack 204 itself may serve as a removably attachable handle instead of fitting within the grip 202. In this manner the battery pack 204 may be easily replaced by the surgeon.

The battery pack 204 has contacts 209 for electrical coupling to an activation switch 210. The activation switch 210 is operated by the depression of a trigger 212 and is electrically coupled to the electronic circuitry 206 via contacts 209. The activation switch 210 is used for controlling the power supplied to a solenoid 214 located above the grip 202 and within the housing 201. The solenoid 214 is electrically coupled to the electronic circuitry by contacts 209. The rear portion of the housing 201 can be opened for access to the compartment by the removal of cap 216 which is threadably attached to the housing 201. Prior to sterilization, the cap 216 and the solenoid 214 can be removed from the housing 201. The rongeur 200 can be sterilized. It is appreciated that all of the electrical components of the electrical rongeur 200 may have contacts 209 such that the electrical components may be easily removed and replaced without the need for wiring these components.

The solenoid 214 drives a reciprocating rod 218 which is removably coupled at its distal end 220 to a cutting/storage member 222 and terminates in a proximal end portion 224. The proximal end portion 224 is made of a non-ferrous material, such that the proximal end portion 224 is not affected by the electromagnetic field generated by the solenoid 214. The rod 218 is spring biased by a strong spring 226 in the proximal direction to maintain the rod 218 in a maximally, proximal position and thus maintain a gap between the foot plate 16 and the cutting edge 22 of the cutting/storage member 222. Near the proximal end portion 224 of the rod 218 is a plunger 228 having a bore 230 for receiving at least a portion of the proximal end portion 224. The plunger 228 is made of a ferrous material such that the plunger 228 is responsive to the electromagnetic field generated by the solenoid 210. When the solenoid 210 is powered, the plunger 228 is driven forward in the distal direction, driving the rod 218 in the same direction toward the foot plate 16 such that the cutting edge 22 of the cutting/storage member 222 contacts the foot plate 16. The rod 218 is then returned to its proximal position by the spring 226. The proximal travel of the plunger 228 is stopped by stopper 232 made of a resilient and sterilizable material such as an appropriate plastic well known by those skilled in the art.

As a safety precaution, the momentum at which the rod 218 is driven forward toward the foot plate 16 may be set to a desired rate, such that excessive force is not exerted on the cutting edge 22 and the foot plate 16. Further, the rod 218 can be adjustable along the longitudinal axis, either by threads or other means, such that a precise closing of the cutting edge 22 against the foot plate 16 is achieved. In this manner, any other tendency of the cutting edge 22 to continue distally placing further stress on the foot plate 16 is avoided.

The depression of the trigger 212 closes the switch 210 to cause one closing and opening of the rongeur 200. For a second closing operation, the trigger 212 must be released and then depressed again in order to close switch 210 once again. A safety mechanism for preventing activation of the switch 210, well known in electrically operated devices, can be included. Such a safety mechanism could consist of a mechanical interference between the trigger and the switch to prevent activation of the switch 210 or a second trigger may be placed in a separate location on the grip 202 to insure that activation of the rongeur occurs only when both the trigger 212 and the second trigger are depressed to avoid accidental activation of the rongeur 200.

Referring to FIGS. 11–14, the cutting/storage member 222 is a hollow tube for containing multiple cut pieces of bone or cartilage, having a sharp cutting edge 22 and an engagement end 234 for removably engaging the rod 218. The cutting/storage member 222 is slidable within a shaft housing 236 which remains stationary as the cutting/storage member 222 reciprocates along the shaft 238 in rectilinear motion. Although the shaft housing 236 has been described and shown as being a single piece, it is appreciated that shaft housing 236 may comprise a number of separate pieces spaced apart along the shaft 238 while still being capable of housing the cutting/storage member 222. Engagement end 234 is closed when in use, but once the cutting/storage member 222 is removed from within the shaft housing 236, it is open such that bone may be pushed from one end of the cutting/storage member 222 out the other end with the use of an obdurator or other similar instrument.

The shaft housing 236 removably engages the shaft 238 in the same manner in which the cutting/storage member 50 (described above) removable attaches to shaft 14 as described in detail above. Like the cutting/storage member 50, the shaft housing 236 has forward rail-engaging members 53,54 which fit within the forward notches 65,66 of shaft 238 and rear rail-engaging members 56,57 which are sufficiently spaced proximally from the forward rail-engaging members 53,54 so that when the forward rail-engaging members 53,54 are placed over forward notches 65,66, the rear rail-engaging members 56,57 are directly over the rear notches 69,71 in the shaft 238. The shaft housing 236 is then slid in the distal direction toward foot plate 16, such that the forward rail-engaging members 53,54 and the rear rail engaging members become engaged to the rails 62,63, and the shaft cover 236 is prevented from sliding upward and becomes locked to the shaft 238.

Referring still to FIG. 11, to ensure that shaft cover 236 stays locked to the shaft 238, a biasing spring 240 is located within the housing 201 and maintains the shaft housing 236 biased in a maximal distal position. During the removal of the shaft housing 236, the shaft housing 236 is moved proximally to compress the biasing spring 240 and permit the shaft housing 236 to become disengaged from the shaft 238.

Figure 14:
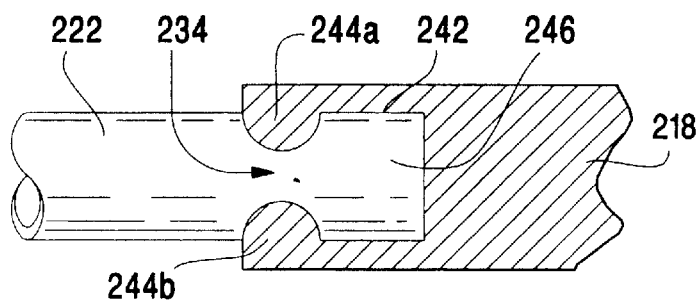
FIG. 14 is a cross sectional view along lines 14—14 of the electrically powered surgical rongeur of FIG. 11.

Referring to FIG. 14, a top plan view of the connections between the cutting/storage member 222 and the rod 218 is shown. The engagement end 234 of the cutting/storage member 222 has a female connection means 242 comprising radiused portions 244a and 244b on both sides such that a corresponding male connection means 246 on the rod 218 fits into the female connection means 242. The cutting/storage member 222 may be engaged to the rod 218 by removing the shaft housing 236 and then lowering the cutting/storage member 222 onto the shaft 238 so that the female and male connection means 242 and 246, respectively, engage. The shaft housing 236 is then replaced and locked to the shaft 238 as described above. To disengage the cutting/storage member 222 from the rod 218, the shaft housing 236 is disengaged from the shaft 238 by sliding the shaft housing 236 in the proximal direction to compress the biasing spring 240, the shaft housing 236 is lifted off, and then the cutting/storage member 222 is easily lifted out.

In use, the surgeon would insert the rongeur 200 around the bone to be cut and the trigger 212 would be pulled. The pulling of the trigger 212 would cause the rod 218 and the cutting/storage member 222 to be driven forward to close against the foot plate 16 cutting the bone and the cutting/storage member 222 and the foot plate 16 are returned to their original open position regardless of the trigger 212 being released or left depressed. This occurs because the delivery of electrical current to the solenoid 214 is interrupted by the electronic circuitry 206 and the strong return spring 226 returns the cutting/storage member 222 and the foot plate 16 to their original open position. Releasing the trigger 212 would permit the cutting/storage member. 222 to return to its open position. The surgeon would then move the rongeur 200, without removing the rongeur 200 from the wound, to the next area of bone requiring biting, and again activate the trigger 212 and cause the rongeur 200 to close. The power rongeur 200 may be modified for use with any of the cutting/storage members described herein, such as the first embodiment described above in reference to FIG. 1.

Figure 15:
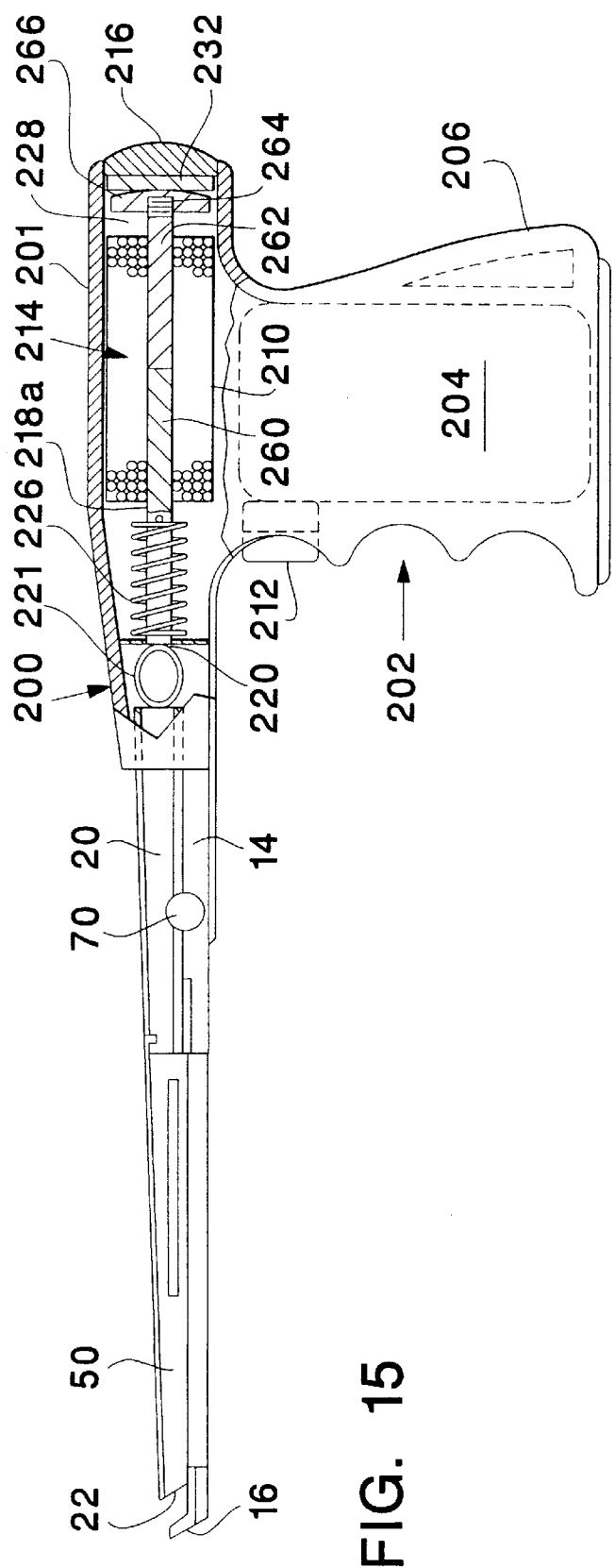
FIG. 15 is an elevational and partial sectional side view of another alternative embodiment of the electrically powered surgical rongeur of the present invention.

Referring to FIG. 15, rongeur 200a is shown which is an alternative embodiment of rongeur 200. In this embodiment, rongeur 200a has a reciprocal rod 218a coupled to the slide drive member 20 by a resilent compressible member 221 described in detail in copending application Ser. No. 07/398, 987 filed on Aug. 28, 1989 incorporated by reference herein. The function of the rongeur 200a is the same as described above for rongeur 10, except that it is powered electrically. It is also appreciated that any of the embodiments of the rongeur of the present invention may be similarly adapted to become electrically powered without departing from the scope of the present invention.

The rod 218a has a non-ferrous portion 260, a ferrous portion 262, and terminates proximally in a threaded end portion 264. Threadably attached to the threaded end portion 264 is a disc 266 which functions to stop the distal travel of the rod 218a as it is advanced through the solenoid 214 by making physical contact with the solenoid 214. As the disc 266 is threadably attached to the threaded end portion 264, the distal travel of the rod 218a may be regulated by varying how far the threaded end portion 264 is threaded into the disc 266 resulting in a change in the length of the rod 218a passing through the solenoid 214. To shorten the distance of the distal travel by the rod 218a, the threaded end portion 264 is threaded further into the disc 266. If a greater distance of travel of the rod 218a is desired, the disc 266 is unscrewed such that less of the threaded end portion 264 is threaded into the disc 266. In this manner, the force generated by the activation of the solenoid 214 is may be adjusted by varying the length of the rod 218a passing through the solenoid 214.

Figure 16:
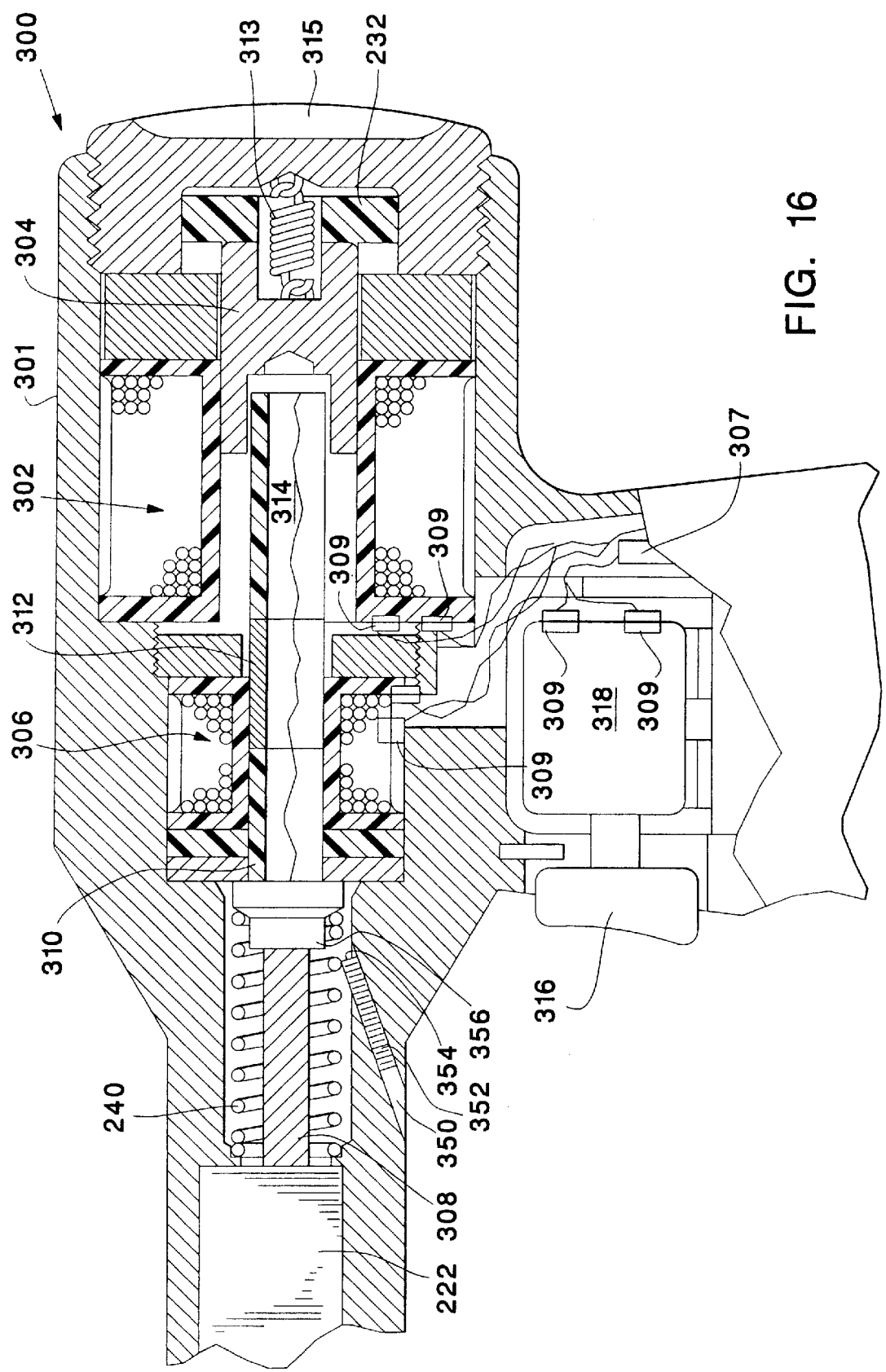
FIG. 16 is a partial elevational and partial sectional side view of another alternative embodiment of the electrically powered surgical rongeur of the present invention.

Referring to FIG. 16, an alternative embodiment of the power rongeur of the present invention is shown and generally referred to by the numeral 300. The rongeur 300 comprises a primary solenoid 302, a plunger 304, a smaller secondary solenoid 306, electronic circuitry 307 and a reciprocating rod 308. The primary solenoid 302, the secondary solenoid 306 and the electronic circuitry 307 are electrically coupled via contacts 309 to facilitate removal and replacement of those components without having to detach and reattach any wires. The reciprocating rod 308 has a proximal end comprising a first nonferrous portion 310, a ferrous portion 312, and a second nonferrous portion 314. The secondary solenoid 306 is much smaller and less powerful than the primary solenoid 302. When the secondary solenoid 306 is activated, the electromagnetic field created urges the reciprocating rod 308 in the distal direction such that the ferrous portion 312 moves distally within the electromagnetic field of the secondary solenoid 306. In this position, the reciprocating rod 308 is positioned in a distal direction sufficient to place the cutting edge 22 of the cutting/storage element 236 (shown in FIG. 11) in contact with the bone to be cut. It is important to note that the purpose of the secondary solenoid 306 is merely to advance the reciprocating rod 308 a sufficient distance to bring the cutting edge 22 in contact with the bone to be cut, but not to cut the bone.

Once the cutting edge 22 is properly positioned at the site in which a cut is desired through the activation of the secondary solenoid 306, the primary solenoid 302 is activated and the plunger 304 is driven in the distal direction to provide a high impact force to the reciprocating rod 308 and the desired cut is performed. At that point in time, the delivery of electrical current to the primary solenoid 302 and the secondary solenoid 304 stops and the reciprocating rod 308 is then returned to its maximal proximal position by the biasing spring 240 regardless of whether the trigger 212 is released or left depressed. The plunger 304 is returned to its starting position by the spring 313 which is coupled to the removable cap 315.

The supply of electrical current to the primary solenoid 302 and secondary solenoid 306 is controlled by a trigger 316 which closes an activation switch 318 having two stages. In the first stage, the trigger 316 is only partially depressed, such that the activation switch 318 delivers electrical current only to the secondary solenoid 306 for positioning the cutting edge 22 against the bone to be cut. The delivery of electrical current to the secondary solenoid 306 ceases immediately upon the release of the trigger 316 permitting the surgeon to reposition the rongeur 300 prior to cutting the bone. In the second stage, the trigger 316 is fully depressed such that the activation switch 318 delivers electrical current to the primary solenoid 302 while continuing to deliver electrical current to the secondary solenoid 306.

The full depression of the trigger 316 causes one closing and opening of the rongeur 300. For a second closing operation, the trigger 316 must be released and then depressed again in order to close switch 210 once again. It is appreciated that the first stage activation of the secondary solenoid 306 may be bypassed if a surgeon desires to make an immediate cut without first positioning the cutting edge 22 against the bone by fully depressing the trigger 316 at once to power the primary solenoid 302.

Further, the electrical rongeur 300 may include a force adjusting means for adjusting the cutting force of the rongeur 300. In one embodiment, such a force adjusting means may include an angled threaded opening 350 in the housing 301 for receiving a threaded member 352 therein. The threaded member 352 is threaded into the opening 350 such that the head 354 of the threaded member 350 sufficiently extends to limit the distal motion of the rod 308 by making contact with the oversized portion 356 of the rod 308. It is appreciated that the further the threaded member 352 is threaded into the opening 350 the greater the limitation of the distal motion of the rod 308 and thus the lesser is the cutting force. It is further appreciated that the cutting force of the rongeur 300 can be limited electronically by controlling the amount of current that is delivered to the primary solenoid 302. Such an electronic means is well known by those skilled in the art.

Referring to FIGS. 17–25, an alternative embodiment of a surgical rongeur made in accordance with the present invention is shown and generally referred to by the numeral 400. The rongeur 400 is similar in structure to the rongeur 10 in the embodiment described above, except that it has an improved button assembly 420 and an improved cutting/storage member 430.

Referring specifically to FIG. 17, the improved button assembly 420 functions to control the displacement of the slide drive member 20 along the shaft 14 in order to release or to engage the cutting/storage member 430 from the shaft 14 as described above. The improved button assembly 420 is located near the proximal end 11 of the shaft 14 and fits in the opening 15 to replace the pivot pin 32. In this manner, the improved button assembly 420 also serves as a pivot pin and attachment means for front handle 30.

Figure 20:
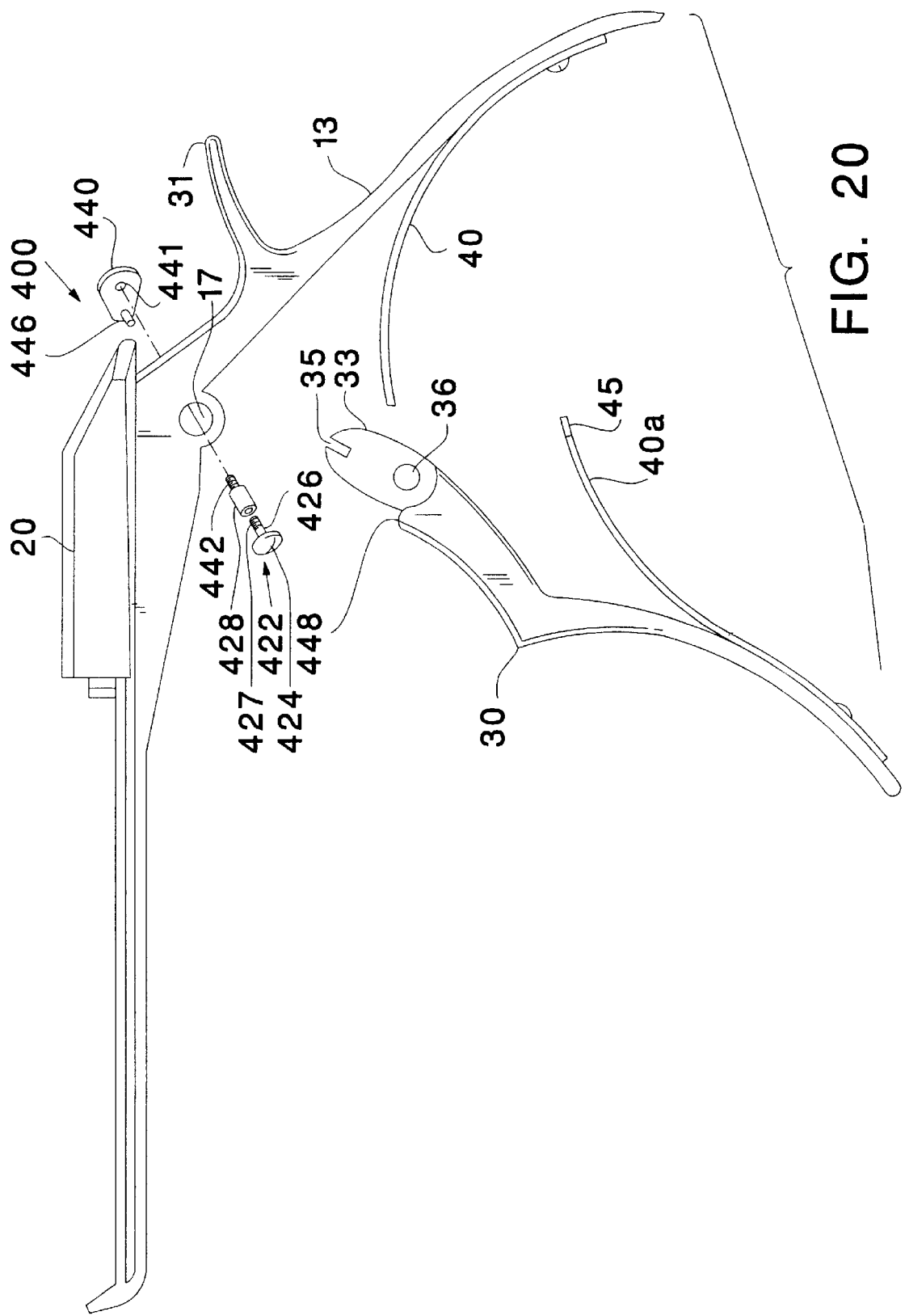
FIG. 20 is a partial, exploded elevational side view of the surgical rongeur of FIG. 17.

Referring to FIG. 20, the improved button assembly 420 comprises a button member 422 having a large diameter portion 424 and a narrow diameter portion 426 with a threaded end 427. The narrow diameter portion 426 fits through a hollow sleeve member 428 and threads to a substantially flat member 440 having a threaded opening 441 and is located on the opposite side of the body 12 of the rongeur 400. The hollow sleeve member 428 acts as a bushing about which the front handle 30 pivots during the operation of the rongeur 400. Between the button member 422 and the substantially flat member 440 is a coiled spring 442 that maintains the button member 422 in a biased position.

Figure 18:
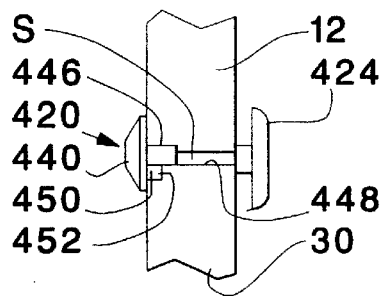
FIG. 18 is a partial elevational front view along view lines 18—18 of the surgical rongeur of FIG. 17 showing the release button in the engaged position.
Figure 19:
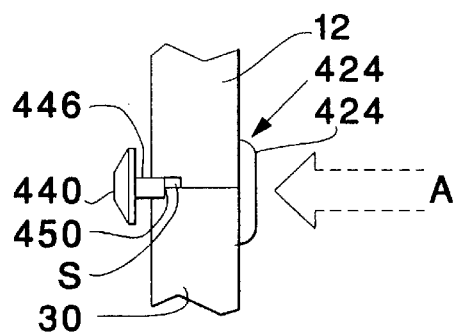
FIG. 19 is a partial elevational front view along view lines 18—18 of the surgical rongeur of FIG. 17 showing the release button in the disengaged position.

Referring to FIGS. 18 and 19, a front elevational view along lines 18—18 of FIG. 17 of the button assembly 420 in the biased position is shown. The substantially flat member 440 has a extension pin 446 that functions to limit the travel of the slide drive member 20 towards the proximal end 11 of the shaft 14. In the biased position, the extension pin 446 is positioned such that it is between the top part 448 of the forward handle 30 and the body 12 to create space S so as to keep the slide drive member 20 in a more distal position. In this manner, the cutting/storage member 430 is engaged to the shaft 14 and is in the locked position as discussed above for the preferred embodiment of the surgical rongeur 10.

Referring to FIG. 19, a front elevational view along lines 18—18 of the button assembly 420 is shown in the unbiased positioned that is achieved when the button assembly 420 is depressed in the direction indicated by arrow A. The top part 448 of the front handle 30 has a notch 450 capable of receiving at least a portion of the extension pin 446 when the button assembly 420 is in the unbiased position. In the unbiased position, the extension pin 446 no longer keeps the top part 448 of the forward handle 30 away from the body 12 of the rongeur 400 such that space S is eliminated and the slide drive member 20 is moved in a more proximal direction which allows the cutting/storage member 430 to be disengaged and removed from the shaft 14. When the extension pin 446 is in the notch 450, the button assembly 420 is prevented from returning to its normal biased position because the wall 452 of the notch 450 prevents the travel of the extension pin 446 in that direction.

When the front handle 30 is squeezed by the surgeon, the front handle 30 moves in the direction of the rear handle 13 and away from the body 12 of the rongeur 400 creating the space S between the top part 448 of the front handle 30 and the body 12. In this position, the extension pin 446 is no longer contained within the notch 450 and moves, as result of the force of the coiled spring 454, into the space S that is created between the top part 448 of the forward handle 30 and the body 12 of the rongeur 400. Once the front handle 30 is released by the surgeon, the top part 448 of the front handle 30 rests against the extension pin 446 and is kept at a distance from the body 12 that is equal to the diameter of the extension pin 446. As a result, the rongeur 400 is self-locking simply by the squeezing of the front handle 30.

Figure 21:
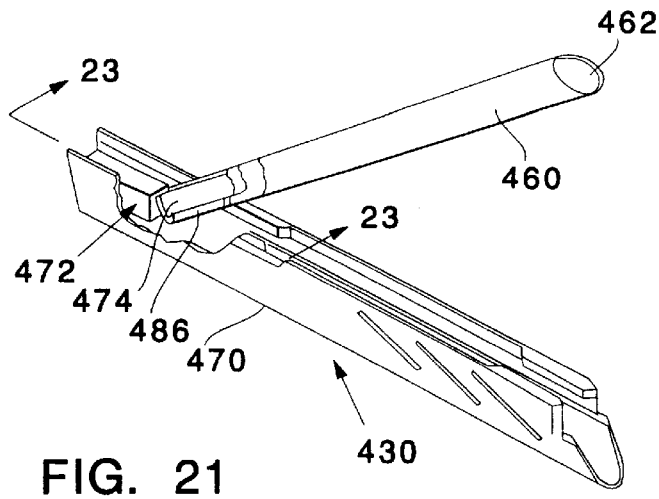
FIG. 21 is a side perspective view of the cutting/storage member of the surgical rongeur of FIG. 17 with the straw member shown in partial cutaway and in the elevated position.
Figure 22:
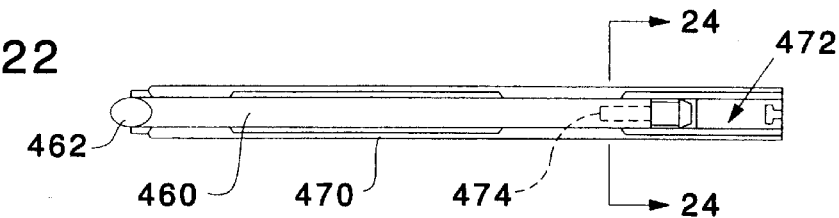
FIG. 22 is a bottom plan view of the cutting/storage member of the surgical rongeur of FIG. 17 with the straw member shown in the lowered position.

Referring to FIGS. 21 and 22, the improved cutting/storage member 430 is shown comprising a removable and disposable straw 460 which is a hollow member that is similar in structure to the straw 90 as described above. The distal end of the straw 460 is a sharp cutting edge 462 for cutting bone or other similar tissue. The straw 460 is affixed to the bottom of a slideable shaft housing 470 which is similar in construction to the carriage member 96 described above but has a straw engagement means 472 for removably engaging the straw 460 to the modified cutting/storage base 470.

Figure 23:
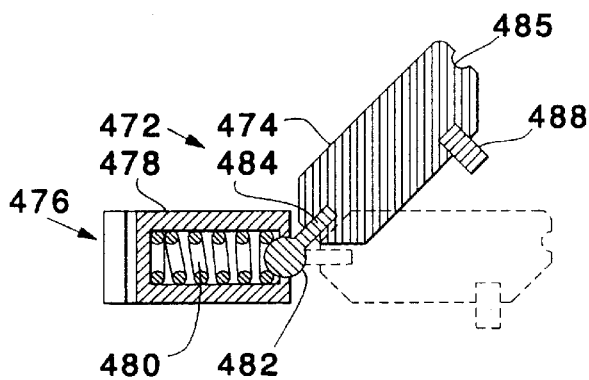
FIG. 23 is a cross sectional view along lines 23—23 of FIG. 21 of the straw engagement means of the cutting/storage member of FIG. 21 shown in the raised position with the lowered position shown in hidden line.

Referring to FIG. 23, an enlarged cross sectional view of the straw engagement means 472 is shown comprising a pivoting member 474 and a detent means 476. The detent means 476 comprises a housing 478 for containing a spring means 480 for spring loading a detent ball 482. A first end 484 of the pivoting member 474 is connected to the detent ball 482 and is maintained by the detent means 476 in a raised position or in a lowered position as shown in broken lines in FIG. 23. A second end 486 of the pivoting member 474 is capable of receiving the proximal end of the straw 460 and has a lip 485 so that the pivoting member 474 may be lifted to the raised position in the absence of a straw 460 in order to permit engagement of the straw 460 to the pivoting member 474.

Figure 24:
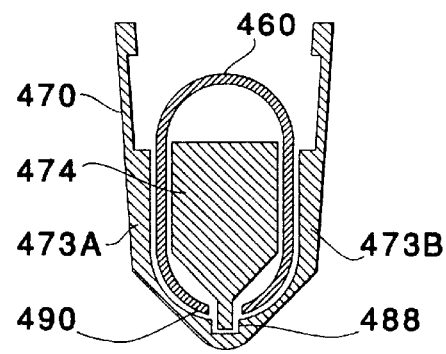
FIG. 24 is a cross sectional view of the cutting/storage member along lines 24—24 of FIG. 22.

Referring to FIG. 24, a cross sectional view of the cutting/storage member 430 along lines 24—24 of FIG. 22 is shown. Extending from the second end 486 of the pivoting member 474 is a stabilizer pin 488 which fits into a corresponding opening 490 located near the proximal end of the straw 460 and functions to stabilize the straw 460 once the pivoting member 474 is inserted within the second end 486 of the straw 460. The stabilizer pin 488 prevents rotational movement and distal movement of the straw 460 during the operation of the rongeur 400.

Referring back to FIG. 21, the straw engagement means 472 functions to facilitate the attachment and the removal of the straw 460 to the shaft housing 470. Prior to use, the straw 460 is placed in the shaft housing 470 so that it engages the pivoting member 474 in the raised position prior to placing the shaft housing 470 on the shaft 14. Once the straw 460 is engaged to the straw engagement means 472, the straw 460 is lowered towards the shaft housing 470 such that the straw 460 wedges into converging trapezoidal walls 473A and 473B and the detent means 476 keeps the straw 460 pressed into a stable wedged position, and prevents any movement of the straw 460 within the shaft housing 470 during the operation of the rongeur 400.

To remove the straw 460, once the shaft housing 470 is removed from the shaft 14, the straw 460 is lifted away from the shaft housing 470 such that the pivoting member 474 is returned to its raised position. The surgeon then simply pulls the straw 460 away from the pivoting member 474 and engages a new straw 460 to the pivoting member 474. The bone contained within the first straw 460 may then be harvested and the first straw 460 may then be disposed.

Figure 25:
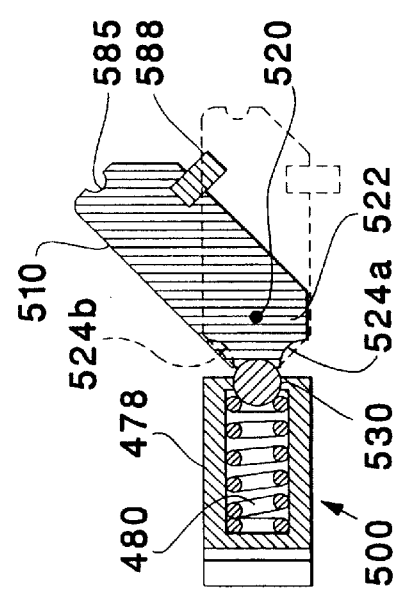
FIG. 25 is a cross sectional view along lines 23—23 of FIG. 21 of an alternative embodiment of the straw engagement means shown in the raised position with the lowered position shown in hidden line.

Referring to FIG. 25, an alternative embodiment of the straw engagement means 500 having a pivoting member 510 that pivots about an axis 520 and has a first end 522 with notches 524*a* and 524*b* each capable of receiving at least a portion of the detent ball 530 therein. The pivoting member 510 has the same function as the pivoting member 474 described above, and the notches 524*a* and 524*b* function to maintain the pivoting member 510 in the lowered or raised position, as described above for the straw engagement means 472. As the pivoting member 570 pivots about the axis 520, the detent ball 530 engages one of the notches 524*a* or 524*b* to hold the pivoting member 570 in a raised or lowered position. The pivoting member 570 has an extension pin 588 that has the same structure and function as the extension pin 488 described above and a lip 585 that has the same structure and function as the lip 485 described above.

Figure 26:
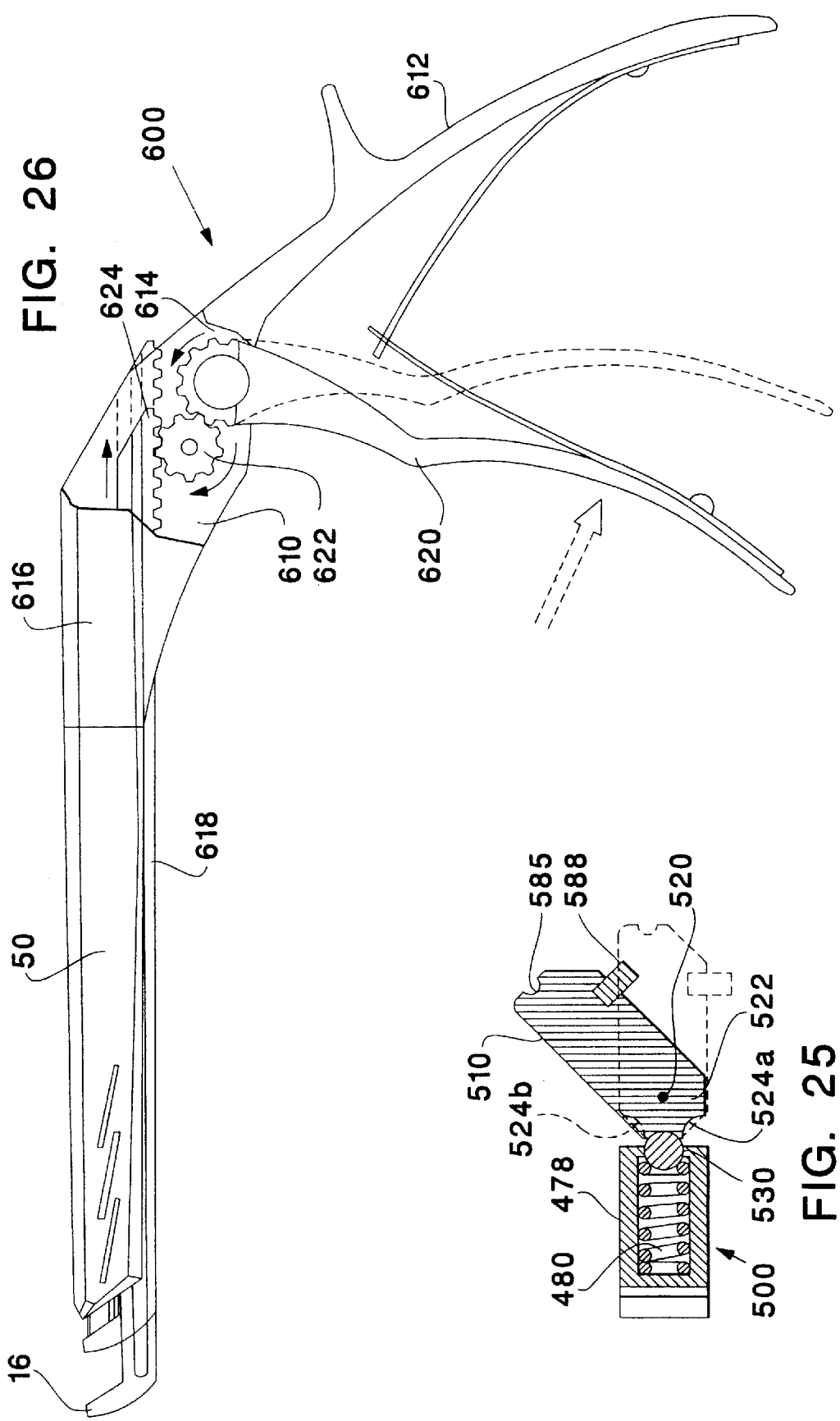
FIG. 26 is a side elevational view of an alternative embodiment of the surgical rongeur of the present invention having a reciprocating shaft terminating in a foot plate and a fixed body portion.

Referring to FIG. 26, an alternative embodiment of the present invention is shown and generally referred to by the numeral 600. The rongeur 600 comprises of a body 610 having a rear handle 612 depending at an angle from the proximal end 614 of the body 610, and has an upper body portion 616 terminating into a removable cutting/storage element 50. The upper body portion 616 is fixed and is capable of housing and slideably receiving a reciprocating shaft 618 which terminates in a foot plate 16. The reciprocating shaft 618 is driven by a front handle 620 which is pivotably attached to the body 610. The front handle 620 drives the reciprocating shaft 618 via a toothed gear 622 which engages a correspondingly toothed track 624 of the reciprocating shaft 618 while the body 610 remains stationary. In this embodiment, the cutting/storage element 50 remains in a fixed position while the shaft 618 reciprocates during the cutting action of the rongeur 600 to bring the foot plate 16 into contact with the cutting/storage member 50.

Referring to FIG. 27, an alternative embodiment of the surgical rongeur of the present invention is shown and generally referred to by the numeral 700. The rongeur 700 comprises a body 712 having a shaft 714 extending distally with a removable portion 715. The removable portion 715 has its distal end terminating in a foot plate 716 and its proximal end having a double-key, male member 718 for engaging a corresponding female member 720 located at the distal end of the shaft 714.

Referring to FIG. 27A, the male member 718 is shown fully seated within the female member 720 to provide a stable coupling capable of enduring the above-described forces encountered during the operation of the rongeur 700.. The removable portion 715 provides the added advantage of allowing the surgeon to easily replace at least a portion of the shaft 714, such as the foot plate 716, along with replacing the cutting/storage member if desired, as described in detail for the embodiments set forth above.

It is appreciated that an important advantage of the removable portion 715 is that multiple removable portions 715 of various sizes and lengths having various foot plates 716 can be made available to the surgeon appropriate for the particular surgical procedure being performed by the surgeon. In this manner the versatility of the rongeur 700 is greatly increased, the need for having multiple rongeurs of different sizes and configurations is eliminated greatly reducing cost, especially if the rongeur 700 is power actuated.

For example, the removable portion 715 may have a foot plate 716 that is angled relative to the shaft 716 in a specific orientation for a particular surgical procedure such that a number customized removable portions 715 may be provided for use with a common body, handle and shaft 714. The removable portion 715 may have different lengths, diameters and the overall configuration of the removable portion 715 may be rounded for use in endoscopic procedures as described in reference to FIGS. 28 and 29 set forth in detail below.

Further, the structure of the rongeur 700 allows for a variety of different sizes and configurations of removable portion 715 and foot plate 716 to be interchangeably utilized with a common handle, body, and shaft 714. Additionally, the structure of the rongeur 700 allows for the replacement of both cutting edges—the cutting/storage member and the foot plate 716—when it is desired to incorporate a cutting surface that is out of the plane of the surface 730 on the foot plate 716 sufficient to provide a cutting surface but not to hold a substantial amount of bone such that it would prevent the bone from being advanced into the cutting/storage member. When the foot plate 716 contains such a cutting surface, it is preferable that the entire removable portion 715 be disposable such that fresh, sharp cutting surfaces are provided with each use.

Referring to FIG. 27B, a partial side sectional view of an alternative embodiment of the rongeur 700 having a foot plate 716*a* with a cutting surface 740 which is out of the plane of the surface 730 of the foot plate 716*a* facing the cutting edge 742 of the cutting/storage member 750 is shown. The cutting surface 740 is slightly raised from the surface 730 such that the cutting surface 730 and the cutting edge 742 contact and mate during the cutting of bone or cartilage. The cutting edge 742 is preferably sharpened only on the interior side 754 of the cutting/storage member 750.

Referring to FIG. 27C, an alternative embodiment of the foot plate 716*a* of FIG. 27B is shown and generally referred to by the numeral 716*b*. The foot plate 716*b* has a cutting surface 740*a* which is out of the plane of the surface 730 facing the cutting edge 742*a* of the cutting/storage member 752. In this embodiment, the cutting surface 740*a* is below the plane of the surface 730 such that the cutting edge 742*a* of the cutting/storage member 752 is received within the cutting surface 740*a*. The cutting edge 742*a* is preferably sharpened on both the interior side 754 and the exterior side 756 such that the cutting edge 742*a* is a knife-like edge.

Referring to FIGS. 28 and 29, an alternative embodiment of the surgical rongeur of the present invention for use in endoscopic surgical procedures is shown and generally referred to by the numeral 800. The endoscopic rongeur 800 has a shaft 814 and a cutting/storage member 850 that are preferably rounded over their entire length, but may be more limitedly rounded in a particular area such as the area of the shaft and handle junction. The cutting/storage member 850 preferably has a straw 890 similar to the straw 90 described above in reference to FIGS. 8 and 9, and having a semi-circular cross section to maximize the biting and storage area of the endoscopic rongeur 800. Such an overall rounded configuration facilitates the passage of the endoscopic rongeur 800 through the skin and flesh or as more commonly practiced through a cannula typically used for such endoscopic surgery to pass through the skin and soft tissue of the patient and into the abdomen, thorax, or within other areas of the body while still allowing for a good seal against gas or fluid leakage from within the body of the patient.

Referring specifically to FIG. 29, a cross sectional view of the endoscopic rongeur 800 is shown illustrating the overall circular diameter of the shaft 814 and cutting/storage member 850. It is appreciated that in order to better form a seal with the opening in the body of the patient, the cutting/storage member 850 may be slideable within a fixed exterior housing, such as shaft housing 236, described above for the embodiment shown in FIGS. 11–14. Such an exterior housing would also have an overall circular diameter. In this manner, once the endoscopic rongeur 800 is placed within the opening in the body, the seal formed between the fixed exterior housing and the opening of the patient is maintained relatively undisturbed.

The endoscopic rongeur 800 preferably has an overall length of approximately 13.0 inches (330.2 mm) to 18.0 inches (457.2 mm), with a shaft length measured from the foot plate to the handle of approximately 10.5 inches (266.7 mm) to 13.0 inches (330.2 mm), and a shaft diameter of approximately 3/16 inches (4.0 mm) to 1/2 inch (12.0 mm), and preferably 1/3 inch (8.0 mm).

It is appreciated that the endoscopic rongeur 800 can be activated manually by rear handle 13 and forward handle 30 described above, having an overall length of approximately 3.5 inches (88.9 mm) to 6.0 inches (152.4 mm). It is further appreciated that the endoscopic rongeur 800 may be power actuated by any of the power means described above in reference to FIGS. 11–16.

Referring to FIGS. 30–32, an alternative embodiment of the surgical rongeur of the present invention is shown and generally referred to by the numeral 900. The rongeur 900 comprises a removable unit 902 which removably engages a body 912. The removable unit 902 comprises a shaft 914 terminating in a foot plate 916 and a cutting/storage member 950. The removable unit 902 has a pair of engagement members 920 and 922 which are identical and fit into corresponding slots 924 and 924 in the body 912. Each of the engagement members 920 and 922 comprise a flexible upper tyne 930 and a flexible lower tyne 932 sufficiently spaced apart to permit the upper and lower tynes 930 and 932 to flex toward each other.

Near the proximal end of the engagement members 920 and 922, each of the upper and lower tynes 930 and 932 have protuberances 934*a* and 934*b* on the external surfaces and radiused portions 936*a* and 936*b* on the interior surfaces to form a substantially circular recess 938. The protuberances 936*a* and 936*b* fit into corresponding notches 940*a* and 940*b* formed in slot 924.

Referring specifically to FIG. 31, engagement member 920 is shown being partially inserted into slot 924 with the upper and lower tynes 930 and 932 being flexed toward each other as a result of the protuberances 934*a* and 934*b* contacting the walls of the slot 924. Located at the end of the slot 924 is a detent means 942 comprising a barrel member 946 connected via shaft 948 to a tab member 952 situated within an opening 956 in the body 912 proximate the slot 924. The detent means 942 is biased distally by spring 954 such that when the proximal ends of the upper and lower tynes 930 and 932 contact the barrel member 946, the spring 956 compresses to permit the upper and lower tynes 930 and 932 to be further inserted into the slot 924 until the protuberances 934*a* and 934*b* coincide in position with the notches 940*a* and 940*b* respectively. As the protuberances 934*a* and 934*b* are entering the notches 940*a* and 940*b*, respectively, the barrel member 946 forces apart the upper and lower tynes 930 and 932, and the spring 956 biases the barrel member 946 distally into the recess 938.

Referring to FIG. 32, engagement member 920 is shown fully inserted and seated within the slot 924 with the protuberances 934*a* and 934*b* fully seated within the notches 940*a* and 940*b*, respectively, and the barrel member 946 is fitted within the recess 938 to maintain the appropriate spacing between the upper and lower tynes 930 and 932 such that the protuberances 934*a* and 934*b* remain fully seated within the notches 940*a* and 940*b*, respectively, and the removable unit 902 is locked into place to the body 912 and can not be removed unless it is unlocked by the surgeon. The removable unit 902 remains locked to the body 912 for as long as the barrel member 946 is situated within the recess 938.

To unlock the removable unit 902 from the body 912, the tabs 952 for each of the engagement members 920 and 922 are moved in the proximal direction by the surgeon such that the barrel member 946 is removed from within the recess 938 and the upper and lower tynes 930 and 932 can be flexed toward each other as the removable unit 902 is pulled away from the body 912 such that the protuberances 934a and 934b exit the notches 940a and 940b, respectively.

The rongeur 900 provides the ideal means for having both cutting elements—the cutting/storage member 950 and the foot plate 916—being replaceable when a second cutting element is present in the form of a raised and sharpened cutting edge on the foot plate 916 sufficient to provide a cutting edge but not to hold a substantial amount of bone such that it would prevent the bone from being advanced into the cutting/storage member 950. When the foot plate 916 contains a cutting edge, it is preferable that the entire end unit 902 be disposable such that fresh, sharp cutting elements are provided with each use.

The rongeur 900 also provides the added advantages of having different sizes and configurations of the removable end unit 902 which can be used with the same body 912 increasing the versatility of the rongeur 900, eliminating the need for having multiple rongeurs of different sizes and configurations and greatly reducing cost, especially if the rongeur 900 is power actuated.

For example, the end unit 902 may have a foot plate 916 that is angled relative to the shaft 916 in a specific orientation for a particular surgical procedure such that a number of specialized end units 902 may be provided for use with the body 912. The end unit may have a shaft 914 and cutting/storage member 950 of different lengths, diameters and the overall configuration of the end unit 902 may be rounded for use in endoscopic procedures as described in reference to FIGS. 28 and 29. In such cases, the entire end unit 902 may be entirely disposable or the end unit 902 may comprise any of the cutting/storage members described above having a disposable portion such as the straw 90 described above in reference to FIGS. 8 and 9.

It is further appreciated that while the body 912 is shown with a manually operated handle, any of the embodiments of the power handles described above in reference to FIGS. 11–16 may be modified to drive the rongeur 900 without departing from the scope of the present invention.

Figure 33:
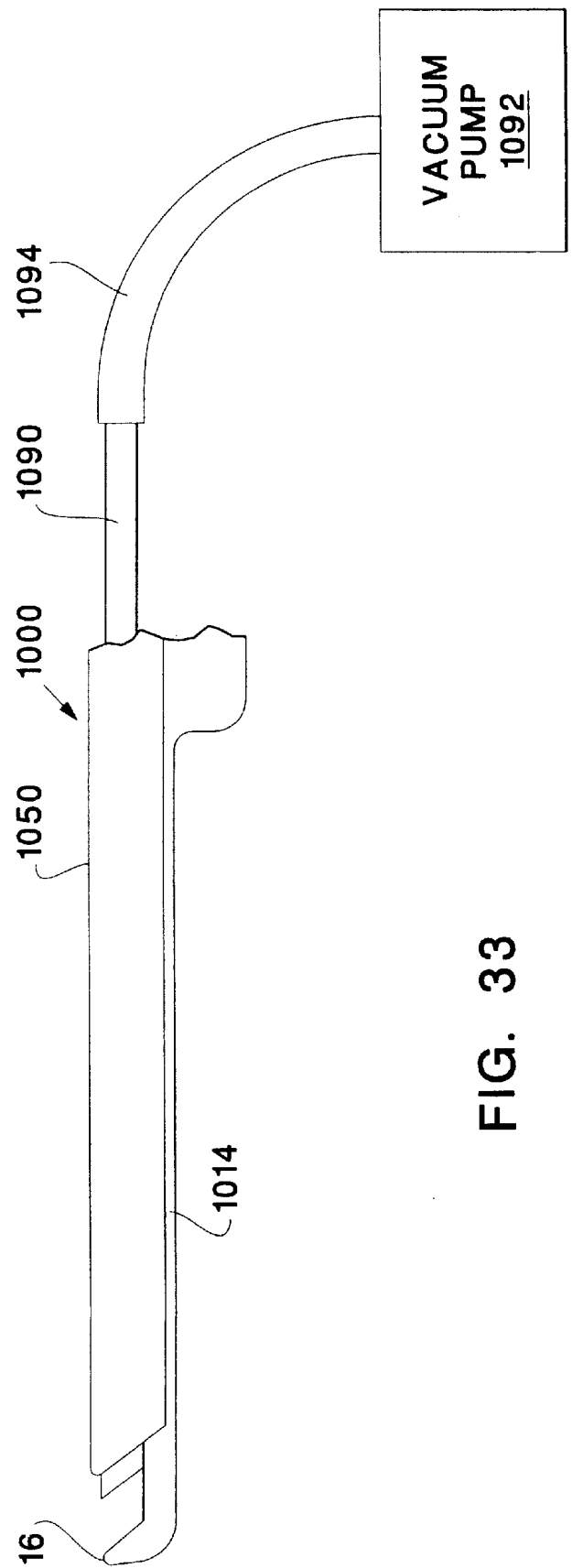
FIG. 33 is a partial elevational side view and schematic diagram of an alternative embodiment of the surgical rongeur of the present invention having a vacuum pump in communication with the cutting/storage member for evacuating any contents of the cutting/storage member.

Referring to FIG. 33, an alternative embodiment of the rongeur of the present invention is shown and generally referred to by the numeral 1000. Rongeur 1000 has a shaft 1014 and a cutting/storage member 1050 that are preferably rounded over their entire length, but may be more limitedly rounded in the area of the shaft and handle junction. The cutting/storage member 1050 preferably has a straw 1090 similar to the straw 90 described above in reference to FIGS. 8 and 9, except that it is in communication with a vacuum pump 1092 via a hose 1094. The vacuum pump 1092 functions to evacuate any cut pieces of bone or cartilage and cogenerated debris from the straw 1090 resulting from the cutting action of the rongeur 1000. The hose 1094 forms an airtight seal with the straw 1090 to prevent vacuum loss and any contamination of the wound with the cut pieces of bone or cartilage or cogenerated debris. The use of a vacuum pump 1092 or similar means well known if by those skilled in the art in association with rongeur 1000 is especially advantageous when the rongeur 1000 is being used in endoscopic surgical procedures where the presence of cut pieces of bone or cartilage and/or. cogenerated debris interferes with the endoscopic procedure.

While the rongeur 1000 has been described with the cutting/storage member 1050 having a straw 1090 in communication with the vacuum pump 1092, it is appreciated that any of the embodiments of the cutting/storage member described above may also be modified to be in communication with vacuum pump 1092 or similar means well known by those skilled in the art to evacuate any cut pieces of bone or cartilage and/or cogenerated debris from the cutting/storage member without departing from the scope of the present invention. While the present invention has been described in association with the preferred embodiment and several alternative embodiments, it is recognized that other variations of the present invention may be made without departing from the scope of the present invention. Further, it is appreciated that any of the manually activated embodiments of the rongeurs described above may also be made to be electrically powered and similarly the electrically powered embodiment may also be made to be manually activated without departing from the scope of the present invention.

What is claimed is:

1. An electrical rongeur for cutting bone or cartilage, comprising:

first and second longitudinally extending shafts capable of reciprocating motion relative to each other, said first shaft terminating in a first jaw portion and said second shaft terminating in a second jaw portion, said first and second jaw portions being in cooperating relationship for cutting bone or cartilage, said second jaw portion adapted to store cut pieces of bone or cartilage in an amount greater than the maximum bone or cartilage capable of being cut in a single cut by said electrical rongeur; and a primary solenoid assembly for activating said reciprocating motion of said first shaft relative to said second shaft whereby said first and second jaw portions close upon activation of said primary solenoid assembly by a primary switch.

2. The electrical rongeur of claim 1 in which each completed activation of said primary solenoid assembly by said primary switch causes a single reciprocating motion between said first and second shafts.

3. The electrical rongeur of claim 2 further including a body for containing said primary solenoid assembly, said body having a closeable opening for accessing said primary solenoid assembly, said primary solenoid assembly being removable and replaceable.

4. The electrical rongeur of claim 3 in which said primary solenoid assembly is electrically coupled to a power source and said primary switch by electrical contacts.

5. The electrical rongeur of claim 1 in which said first and second shafts are returned to a preactivation starting position after each completed activation of said primary solenoid assembly regardless of the position of said primary switch.

6. The electrical rongeur of claim 1 further comprising a secondary solenoid assembly for moving at least one of said first and second shafts for positioning said first and second jaw portions at a site at which a cut is desired, said secondary solenoid assembly being activated by a secondary switch.

7. The electrical rongeur of claim 6 in which said primary and secondary switches are a dual stage switch in which a first stage activates said secondary solenoid assembly and a second stage activates at least said primary solenoid assembly.

8. The electrical rongeur of claim 6 in which said primary solenoid assembly can only be activated while said secondary solenoid assembly is activated.

9. The electrical rongeur of claim 6 in which said primary and secondary switches cease the delivery of electrical current immediately following the completed activation of said primary and secondary solenoid assemblies and said first and second shafts are returned to a preactivation starting position.

10. The electrical rongeur of claim 1 in which said primary solenoid assembly is battery powered.

11. The electrical rongeur of claim 10 in which said battery is a replaceable and an integral part of said electrical rongeur.

12. The electrical rongeur of claim 11 in which said battery is at least a part of a handle for said electrical rongeur.

13. The electrical rongeur of claim 12 in which said first and second shafts comprise first detachable and replaceable portions.

14. The electrical rongeur of claim 13 in which said detachable and replaceable portions are replaceable as a unit.

15. The electrical rongeur of claim 14 further comprising a lock for locking said unit to said solenoid assembly.

16. The electrical rongeur of claim 13 further comprising a second detachable and replaceable portion having a different configuration than said first detachable and replaceable portions.

17. The electrical rongeur of claim 16 in which at least a portion of said detachable and replaceable portions are disposable.

18. The electrical rongeur of claim 17 in which said first portion is a foot plate having a front surface facing said second jaw portion, said front surface being in a first plane and having a cutting surface in a second plane different than said first plane.

19. The electrical rongeur of claim 13 in which at least one of said first and second shafts is removably attached to said solenoid assembly.

20. The electrical rongeur of claim 19 in which said first and second shafts are removably attached as a unit from said solenoid assembly.

21. The electrical rongeur of claim 19 further comprising a third removably attachable shaft having a different configuration than said at least one removably attached first and second shafts.

22. The electrical rongeur of claim 19 in which said first jaw portion is a foot plate having a front surface facing said second jaw portion, said front surface being in a first plane and having a cutting surface in a second plane different than said first plane.

23. The electrical rongeur of claim 1 in which said first portion is a foot plate having a front surface facing said second jaw portion, said front surface being in a first plane and having a cutting surface in a second plane different than said first plane.

24. The electrical rongeur of claim 1 including a shaft cover coupled to said first shaft wherein at least a portion of said second shaft passes through said shaft cover.

25. The electrical rongeur of claim 1 including a force adjustor for adjusting the cutting force of said electrical rongeur.

26. The electrical rongeur of claim 25 in which said force adjustor comprises a screw for limiting the distal excursion of a plunger passing through said primary solenoid assembly, whereby the length of said plunger passing through said primary solenoid assembly is adjusted.

27. The electrical rongeur of claim 25 in which said force adjustor includes a regulator for varying the amount of electrical current supplied to said primary solenoid assembly.

28. The electrical rongeur of claim 1 in which said first jaw portion is a foot plate.

29. The electrical rongeur of claim 28 in which said foot plate includes a cutting element.

30. The electrical rongeur of claim 29 in which said second jaw portion is a combined cutting element and storage member capable of taking multiple maximum bites of bone or cartilage, said maximum bites being defined by the maximum cutting capacity of said cutting element, and said bites being safely stored in said storage member throughout the procedure of cutting bone or cartilage.

31. The electrical rongeur of claim 30 in which at least a portion of said combined cutting element and storage member is disposable.

32. The electrical rongeur claim 1 in which said second jaw portion is a combination cutting element and storage member.

33. The electrical rongeur of claim 32, further comprising a lock for locking said combined cutting element and storage member to at least one of said first and second shafts.

34. The electrical rongeur of claim 33 in which said lock comprises a controller for controlling the displacement of said second shaft relative to said first shaft; said controller configured to permit said combined cutting element and storage member to be unlocked from at least one of said first and second shafts when the displacement of said second shaft relative to said first shaft beyond a maximum extent possible during use of said rongeur.

35. The electrical rongeur of claim 34 in which said controller comprises a button assembly.

36. The electrical rongeur of claim 1 including a slidable shaft housing removably attachable to said second shaft, said shaft housing having a holder for holding a combined cutting element and storage member, said combined cutting element and storage member having a cutting edge at its distal end proximate said foot plate and a storage chamber proximate said cutting edge for collecting and storing cut pieces of bone or cartilage.

37. The electrical rongeur of claim 1 in which said first and second shafts have an external configuration which is substantially rounded for use in endoscopic surgical procedures.

38. The electrical rongeur of claim 1 including means for forming a seal against gas or fluid leakage from within the body of a patient through which said rongeur passes during endoscopic surgical procedures.

39. A rongeur for cutting bone or cartilage, comprising:
a body, said body having a handle portion:
first and second longitudinally parallel shafts capable of reciprocal motion relative to each other, said first shaft terminating distally in a footplate having a first sharpened cutting surface, said footplate being removeably attachable to a proximal portion of said first shaft;
said second shaft terminating in a second sharpened cutting surface, said second sharpened cutting surface being removeably attachable to a proximal portion of said second shaft; whereby the reciprocal motion of said first and second shafts relative to each other brings the first and second sharpened cutting surfaces in opposition to each other to cut bone and cartilage;
a primary solenoid assembly for activating said reciprocating motion of said first shaft relative to said second shaft where said first and second jaw portions close upon activation of said primary solenoid assembly by a primary switch; and
a secondary solenoid assembly for moving at least one of said first and second desired, said secondary solenoid assembly being activated by a secondary switch.

* * * * *

UNITED STATES PATENT AND TRADEMARK OFFICE

CERTIFICATE OF CORRECTION

PATENT NO: 6,142,997

DATED: November 7, 2000

INVENTOR: Gary Karlin Michelson

It is hereby certified that an error appears in the above-identified patent and that said Letters Patent is hereby corrected as shown below:

Column 28, Claim 39, penultimate line: after "second" insert --shafts for positioning said first and second jaw portions at a site at which a cut is--.

Signed and Sealed this

Eighth Day of May, 2001

*Attest:*

NICHOLAS P. GODICI

*Attesting Officer*   Acting Director of the United States Patent and Trademark Office